(12) United States Patent
Koh et al.

(10) Patent No.: US 7,149,579 B1
(45) Date of Patent: Dec. 12, 2006

(54) SYSTEM AND METHOD FOR DETERMINING PATIENT POSTURE BASED ON 3-D TRAJECTORY USING AN IMPLANTABLE MEDICAL DEVICE

(75) Inventors: Steve Koh, South Pasadena, CA (US); Mark W. Kroll, Simi Valley, CA (US); Euljoon Park, Valencia, CA (US); Gene A. Bornzin, Simi Valley, CA (US)

(73) Assignee: Pacesetter, Inc., Sylmar, CA (US)

( * ) Notice: Subject to any disclaimer, the term of this patent is extended or adjusted under 35 U.S.C. 154(b) by 698 days.

(21) Appl. No.: 10/329,233

(22) Filed: Dec. 23, 2002

(51) Int. Cl.
*A61N 1/00* (2006.01)
(52) U.S. Cl. ........................................ 607/19
(58) Field of Classification Search .................. 607/17; 600/585, 587, 595
See application file for complete search history.

(56) References Cited

U.S. PATENT DOCUMENTS

| | | | |
|---|---|---|---|
| 5,233,984 A | 8/1993 | Thompson | 607/18 |
| 5,330,510 A | 7/1994 | Legay et al. | 607/19 |
| 5,593,431 A | 1/1997 | Sheldon | 607/19 |
| 5,957,957 A | 9/1999 | Sheldon | 607/17 |
| 6,002,963 A | 12/1999 | Mouchawar et al. | 607/18 |
| 6,044,297 A | 3/2000 | Sheldon et al. | 607/17 |
| 6,307,481 B1 | 10/2001 | Lehrman et al. | 340/669 |
| 6,356,085 B1 | 3/2002 | Ryat et al. | 324/658 |

FOREIGN PATENT DOCUMENTS

WO    WO 96/30080    10/1996

OTHER PUBLICATIONS

Marmarelis, V.Z, "*Identification of Nonlinear Biological Systems Using Laguerre Expansions of Kernels*", Annals of Biomedical Engineering, vol. 21, pp. 573-589 (1993).

*Primary Examiner*—Mark Bockelman

(57) ABSTRACT

Time-varying spatial signals are detected by accelerometers mounted within the patient. The signals, representative of the actual 3-D trajectory of the patient, are compared with information representative of expected trajectories retrieved from memory to identify a current patient posture, which may be either a dynamic posture such as walking or running or a change in posture such as rising from a seated position to a standing position. In this manner, a change in posture of the patient is identified based upon a full 3-D trajectory, rather than merely the orientation of the patient at the beginning and the end of the change in posture. In an example described herein, the implantable device stores information representative of expected 3-D trajectories in the form of pre-calculated comparison matrices derived from orthonormal kernels employing Laguerre functions or Lagrange functions. A technique is also described for use by an external programmer for pre-calculating comparison matrices so as to reduce the processing burden within the implanted device during posture detection.

22 Claims, 10 Drawing Sheets

US 7,149,579 B1

SYSTEM AND METHOD FOR DETERMINING PATIENT POSTURE BASED ON 3-D TRAJECTORY USING AN IMPLANTABLE MEDICAL DEVICE

CROSS-REFERENCE TO RELATED APPLICATIONS

This application is related to U.S. patent application Ser. No. 10/328,642, titled "System and Method for Determining Patient Posture Based on 3-D Trajectory Using an Implantable Medical Device," filed concurrently herewith.

FIELD OF THE INVENTION

The invention generally relates to implantable medical devices, such implantable stimulation devices and, in particular, to techniques for detecting the posture of the patient in which the device is implanted.

BACKGROUND OF THE INVENTION

Various medical devices are designed for surgical implantation into humans or animals. One common example is the cardiac pacemaker, which recognizes various dysrhythmias such as an abnormally slow heart rate (bradycardia) or an abnormally fast heart rate (tachycardia) and delivers electrical pacing pulses to the heart in an effort to remedy the dysrhythmias. Another is the implantable cardioverter-defibrillator ("ICD"), which additionally (or alternatively) recognizes atrial fibrillation (AF) or ventricular fibrillation (VF) and delivers electrical shocks to terminate the fibrillation. Pacemakers, ICDs and related devices for stimulating heart tissue are generally referred to as implantable cardiac stimulation devices. Other types of implantable medical devices include non-cardiac stimulation devices for stimulating or sensing portions of the brain, spinal cord, muscles, bones, nerves, glands or other body organs or tissues.

Within the implantable medical devices, particularly pacemakers and ICDs, it is often desirable to be able to detect the degree of activity of the patient in which the device is implanted, i.e. to determine whether the patient is standing, walking briskly, running, or walking up stairs. For example, within patients whose cardiac system is incapable of responding to an increase in physical activity, it is desirable to control the pacemaker to elevate the pacing rate while the patient is engaged in any potentially strenuous physical activity. Pacemakers that are responsive to the degree of activity of the patient are generally referred to as rate-responsive pacemakers. One technique for detecting the degree of activity of the patient is to employ one or more accelerometers that are responsive to the movement of the patient. A discussion of rate-responsive pacemakers and accelerometers for use therein is provided in U.S. Pat. No. 6,002,963 to Mouchawar et al., entitled "Multi-Axial Accelerometer-Based Sensor For An Implantable Medical Device And Method Of Measuring Motion Measurements Therefor", Dec. 14, 1999, which is incorporated by reference herein in its entirety.

However, for some patients and under some circumstances, merely detecting the degree of activity the patient is not sufficient. For example, it may be desirable to provide a higher pacing rate while standing still than while sitting still even though the degree of activity is the same. However, a conventional activity sensor, which merely detects the degree of motion the patient, is not typically capable of distinguishing between the standing still and sitting still. Accordingly, it is also desirable to be able to detect the current posture of the patient, i.e. whether the patient is lying down, sitting or standing. One technique for detecting the current posture the patient is to employ a multi-axial accelerometer, of the type described in the patent cited above, which is capable of determining the orientation of the patient and is, in particular, capable of distinguishing between a prone patient and a standing patient based on the relative orientation of the accelerometer. However, such techniques are not entirely reliable when distinguishing between a seated posture and a standing posture, since the torso of the patient is typically oriented vertically in both cases. Accordingly, the device may erroneously determine that the patient is standing, rather than sitting, and provide an unnecessarily high pacing rate or, worse, the device may erroneously determine that the patient is sitting, rather than standing, and thereby providing a pacing rate that is too low, resulting in possible dizziness or feinting of the patient.

Accordingly, it would be desirable to provide improved techniques for reliably detecting the posture of the patient using an implantable medical device and it is to this and that aspects of invention are directed.

Moreover, in many circumstances, merely detecting in the posture of the patient is insufficient. Rather, it is preferable to detect a change in posture of the patient and to provide a temporary increase in heart rate when the patient changes posture in such a way as to require higher heart output. For example, it is desirable to temporarily increase the heart rate just as the patient rises from a seated position to a standing position to prevent dizziness or fainting, which might otherwise occur as a result of the inability of the heart of the patient to properly respond to the change in posture. Hence, devices that merely detect the current posture of the patient, even if achieved reliably, do not provide optimal functionality.

One possible technique for detecting a change in posture of the patient (which is not necessarily prior art to the present invention) is to detect the current posture following every burst of activity of the patient and then to compare the current posture with the last-known posture to thereby detect a change in posture. For example, if after a burst of activity, the device detects that the patient is now standing and the device had previously determined that the patient was sitting, and then the device can then conclude that the patient has stood up from a seated position and can increase the heart rate temporarily to prevent dizziness. However, for this technique to work reliably, the current posture and the previous posture must both be reliably and independently detected. Any error in the detection of either the current posture or the previous posture results in an erroneous detection of the change in posture, which, in turn, can result a pacing rate which is either too high or too low. As has already been mentioned, it can be difficult using conventional techniques to reliably detect the current posture and, in particular, to distinguish between sitting in standing. Accordingly, it is even more difficult to reliably identify a change in posture. In particular, since it is difficult for conventional techniques to distinguish between the seated posture and the standing posture, it is quite difficult to reliably detect when the patient rises from a seated position, again resulting in potentially adverse consequences if the proper pacing rate is not provided.

Accordingly, it would also be desirable to provide improved techniques for reliably detecting a change in posture of the patient using an implantable medical device and, in particular, for reliably detecting change in posture without a prior knowledge of the last posture and it is to this end that further aspects of invention are directed.

Additionally, once provided with a more reliable technique for detecting the current posture or change in posture of the patient, it would be desirable to provide enhanced medical device functionality that exploits the determination and it is to this end that still further aspects of invention are directed. For example, within ICDs, which deliver cardioversion shocks upon detection of atrial fibrillation, it would be desirable to selectively inhibit the delivery of such shocks based on the current posture or change in posture of the patient to better ensure the safety of the patient. In particular, it would be desirable to provide a technique for inhibiting the delivery of cardioversion shocks if the patient is found to be ascending or descending a staircase, as the delivery of such a shock at that time could result in serious injury.

Although the aforementioned concerns have been described primarily with reference to pacemakers and ICDs, similar or related concerns arise with respect to any implantable medical device requiring reliable detection of the current posture or change in posture of the patient and so it is desirable to provide improved techniques which can be exploited within a wide range of implantable medical devices.

Finally, given the processing, memory, and power of limitations inherent within implantable medical devices, it is desirable to provide techniques for permitting the aforementioned improvements to be most efficiently exploited within the implantable medical device, and still other aspects of invention are directed to that end. In particular, it would be desirable to provide set-up techniques for pre-calculating within an external programmer much of the information that the implantable medical device might require for posture determination such that the information may then be transmitted to the implantable device for use therein to reduce the resources required within the actual implantable device. Preferably, the pre-calculated information is specific to the particular patient. Still other aspects of the invention are directed to these ends.

SUMMARY OF THE INVENTION

In accordance with a first aspect of the invention, a technique is provided for use within an implantable medical device for identifying the posture of a patient in which the device is implanted based on time-varying signals representative of the trajectory of the patient. The technique is capable of detecting dynamic postures such as walking on a level surface, walking up stairs, walking down stairs, running, and pedaling, as well as changes in posture such as sitting to standing, standing to sitting, rising from a prone position, reclining to a prone position, rolling over while in a prone position, and sudden falling. Once a change in posture has been detected, the technique thereby also detects the resulting static posture such as sitting, standing, or lying prone. Herein, where appropriate, the term "patient posture" is used to generally refer to any of the aforementioned types of patient postures including static postures, dynamic postures, and changes in posture.

Preferably, time-varying 3-D acceleration signals are detected, which are then integrated to yield the 3-D spatial trajectory of the patient. Information representative of trajectories associated with postures of interest is retrieved from memory. Then, patient posture is identified based on a comparison of the 3-D spatial trajectory of the patient and the information retrieved from memory. In this manner, the patient posture is identified based upon the full 3-D trajectory of the patient, rather than merely the orientation of the patient. By exploiting the full 3-D trajectory of the patient, the technique thereby more reliably detects changes in posture of the type wherein the initial and final orientations of the torso of the patient are similar, such as occur when the patient rises from a seated position to a standing position or vice versa. Moreover, by exploiting the full 3-D trajectory of the patient, the device need not compare the current posture with a previously determined posture. Hence, no a priori knowledge of previous posture is required and problems that might otherwise arise as a result of misidentification of a previous posture do not affect the detection of the current posture. In addition, since the trajectory leading to the current posture is detected, the device can more reliably distinguish between postures with similar chest orientation such as sitting vs. standing. More specifically, the trajectory leading to a standing position is significantly different from the trajectory leading to a seated position.

The implantable medical device may be, for example, a cardiac stimulation device such as a pacemaker or ICD. Within pacemakers, the pacing rate may be controlled based upon either the current posture or the change in posture. Within ICDs, the delivery of cardioversion therapy may be enabled or inhibited based upon the current posture or change in posture. Posture detection processing is preferably triggered only upon detection of a substantial change in the level of activity of the patient.

In a first exemplary embodiment, the device is configured to detect a particular change in posture, such as determining whether the patient has fallen. The implantable device has a memory that preferably stores information representative of 3-D spatial trajectories expected to occur during a particular change in posture in the form of a comparison matrix Z wherein $Z=(H^T*H)^{-1}*H^T$ where H is a matrix of orthonormal kernels ($K_1$, $K_2$, $K_3$) each representing the expected motion of the accelerometer along an orthonormal axis during the particular change in posture. The orthonormal kernels may be represented by, for example, Laguerre functions or Lagrange functions. The 3-D spatial trajectory is represented by orthonormal time-series position vectors ($P_1$, $P_2$, $P_3$) collectively comprising a position matrix P. The device detects the current change in posture by determining whether P sufficiently matches H by evaluating a correction vector C wherein C=Z*P. In one specific example, the device determines whether P sufficiently matches H by calculating a distance D from the correction vector C to a vector I wherein I=[1,1,1] and then determining whether the distance D is less than a predetermined threshold distance. In another specific example, the device determines whether P sufficiently matches H by calculating a distance D from the correction vector C to a pre-stored vector A, wherein A represents an average of a cluster of C vectors previously calculated for the particular patient during previous instances of the change in posture to be detected. The distance D is then compared with a predetermined threshold distance.

In a second exemplary embodiment, the device is configured to distinguish among a plurality of possible changes in posture. The implantable device has a memory that preferably stores information representative of 3-D spatial trajectories associated with various changes in posture in the form of a set of n comparison matrices $Z_n$ wherein $Z^n=(H_n^T*H_n)^{-1}*H_n^T$ where $H_n$ is a set of n matrices of orthonormal kernels ($K_{1n}$, $K_{2n}$, $K_{3n}$) each representing the expected motion of the accelerometer along an orthonormal axis during an nth change in posture out of N total changes in posture. Again, the orthonormal kernels are preferably represented by Laguerre functions or Lagrange functions. The device determines which $H_n$ most closely matches $P_n$ by evaluating a set of correction vectors $C_n$ wherein $C_n=Z_n*P$.

In accordance with a second aspect of the invention, a technique is provided for use by an external programmer device for use with an implantable medical device for implant within a patient wherein the implantable medical device includes a trajectory-based posture detection system. The method is provided for generating patient-specific trajectory-based posture detection information for transmission to the implantable device for use therein in the detection of patient posture. In one example, the method generates information representative of patient-specific corrections between expected 3-D spatial trajectories and actual 3-D trajectories derived for the particular patient. To this end, information representative of the 3-D spatial trajectories expected to occur during a particular change in posture is retrieved from a memory. Information representative of a plurality of actual 3-D trajectories of the patient detected while the patient repeatedly performs the change in posture are received from the implanted device. A posture determination set-up system then generates information representative of patient-specific corrections between the 3-D spatial trajectories expected to occur and the actual 3-D trajectories of the patient. The information representative of 3-D spatial trajectories expected to occur and the information representative of the patient-specific corrections are then transmitted to the implantable device such that the implantable device can thereafter use the information to identify patient posture based on actual 3-D trajectories detected for the patient. The technique may be performed, for example, by an external programmer in communication with a pacemaker or ICD. Control parameters for controlling the operation of the implantable device based on patient posture are also transmitted to the implantable device.

By generating the information representative of patient-specific corrections within the external programmer then transmitting the information to the implanted device, the implanted device need not devote resources to these potentially processor- and memory-intensive procedures. Moreover, a physician can control the manner by which the implanted device responds to particular postures or changes in posture.

BRIEF DESCRIPTION OF THE DRAWINGS

Further features and advantages of the present invention may be more readily understood by reference to the following description taken in conjunction with the accompanying drawings, in which.

DESCRIPTION OF THE PREFERRED EMBODIMENTS

The following description includes the best mode presently contemplated for practicing the invention. The description is not to be taken in a limiting sense but is made merely for the purpose of describing the general principles of the invention. The scope of the invention should be ascertained with reference to the issued claims. In the description of the invention that follows, like numerals or reference designators will be used to refer to like parts or elements throughout.

Referring to remaining figures, exemplary posture detection techniques will now be described. Initially, an overview of an implantable cardiac stimulation device is provided with reference to FIGS. 1 and 2 and an overview of an external programmer used to program the device is then provided with reference to FIG. 3. However, it should be understood that the posture detection techniques of the invention are applicable to other implantable medical devices as well. Then, with reference to FIGS. 4–7, techniques are described for detecting a particular posture. Techniques are described for discriminating among a various possible postures, with reference to FIGS. 8 and 9. Finally, a set-up technique is described with reference to FIG. 10 for use by the external programmer of FIG. 3 for pre-calculating data in advance for subsequent use be the implantable device to thereby reduce resource demands within the implantable device.

Implantable Device Overview

Figure 1:
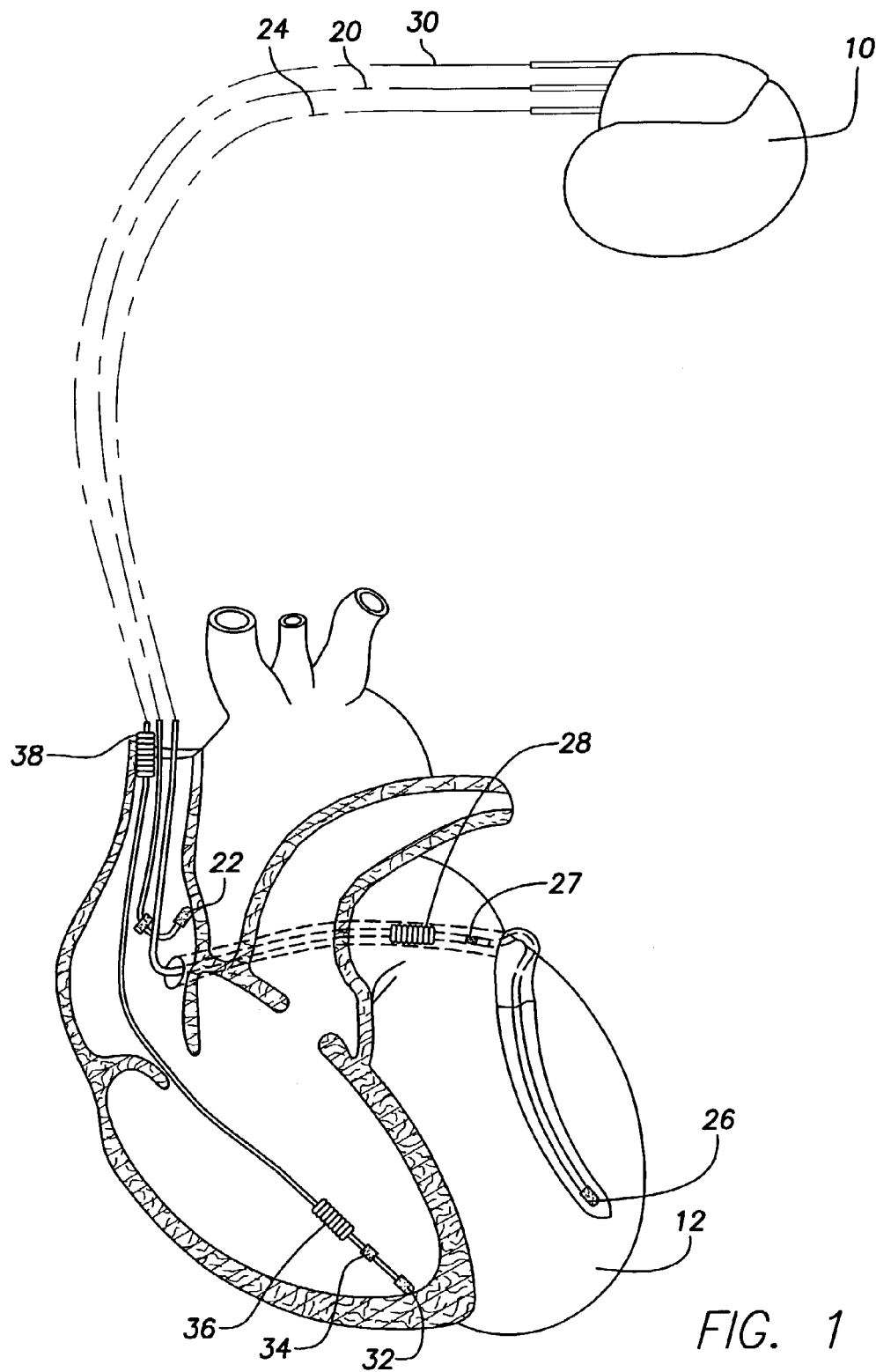
FIG. 1 is a simplified diagram illustrating an implantable stimulation device in electrical communication with at least three leads implanted into the heart of a patient for delivering multi-chamber stimulation and shock therapy.

As shown in FIG. 1, there is a stimulation device 10 in electrical communication with a patient's heart 12 by way of three leads, 20, 24 and 30, suitable for delivering multi-chamber stimulation and shock therapy. To sense atrial cardiac signals and to provide right atrial chamber stimulation therapy, the stimulation device 10 is coupled to an implantable right atrial lead 20 having at least an atrial tip electrode 22, which typically is implanted in the patient's right atrial appendage.

To sense left atrial and ventricular cardiac signals and to provide left chamber pacing therapy, the stimulation device 10 is coupled to a "coronary sinus" lead 24 designed for placement in the "coronary sinus region" via the coronary sinus os for positioning a distal electrode adjacent to the left ventricle and/or additional electrode(s) adjacent to the left atrium. As used herein, the phrase "coronary sinus region" refers to the vasculature of the left ventricle, including any portion of the coronary sinus, great cardiac vein, left marginal vein, left posterior ventricular vein, middle cardiac vein, and/or small cardiac vein or any other cardiac vein accessible by the coronary sinus.

Accordingly, an exemplary coronary sinus lead 24 is designed to receive atrial and ventricular cardiac signals and to deliver left ventricular pacing therapy using at least a left ventricular tip electrode 26, left atrial pacing therapy using at least a left atrial ring electrode 27, and shocking therapy using at least a left atrial coil electrode 28.

The stimulation device 10 is also shown in electrical communication with the patient's heart 12 by way of an implantable right ventricular lead 30 having, in this embodiment, a right ventricular tip electrode 32, a right ventricular ring electrode 34, a right ventricular (RV) coil electrode 36, and an SVC coil electrode 38. Typically, the right ventricular lead 30 is transvenously inserted into the heart 12 so as to place the right ventricular tip electrode 32 in the right ventricular apex so that the RV coil electrode will be positioned in the right ventricle and the SVC coil electrode 38 will be positioned in the superior vena cava. Accordingly, the right ventricular lead 30 is capable of receiving cardiac signals, and delivering stimulation in the form of pacing and shock therapy to the right ventricle.

Figure 2:
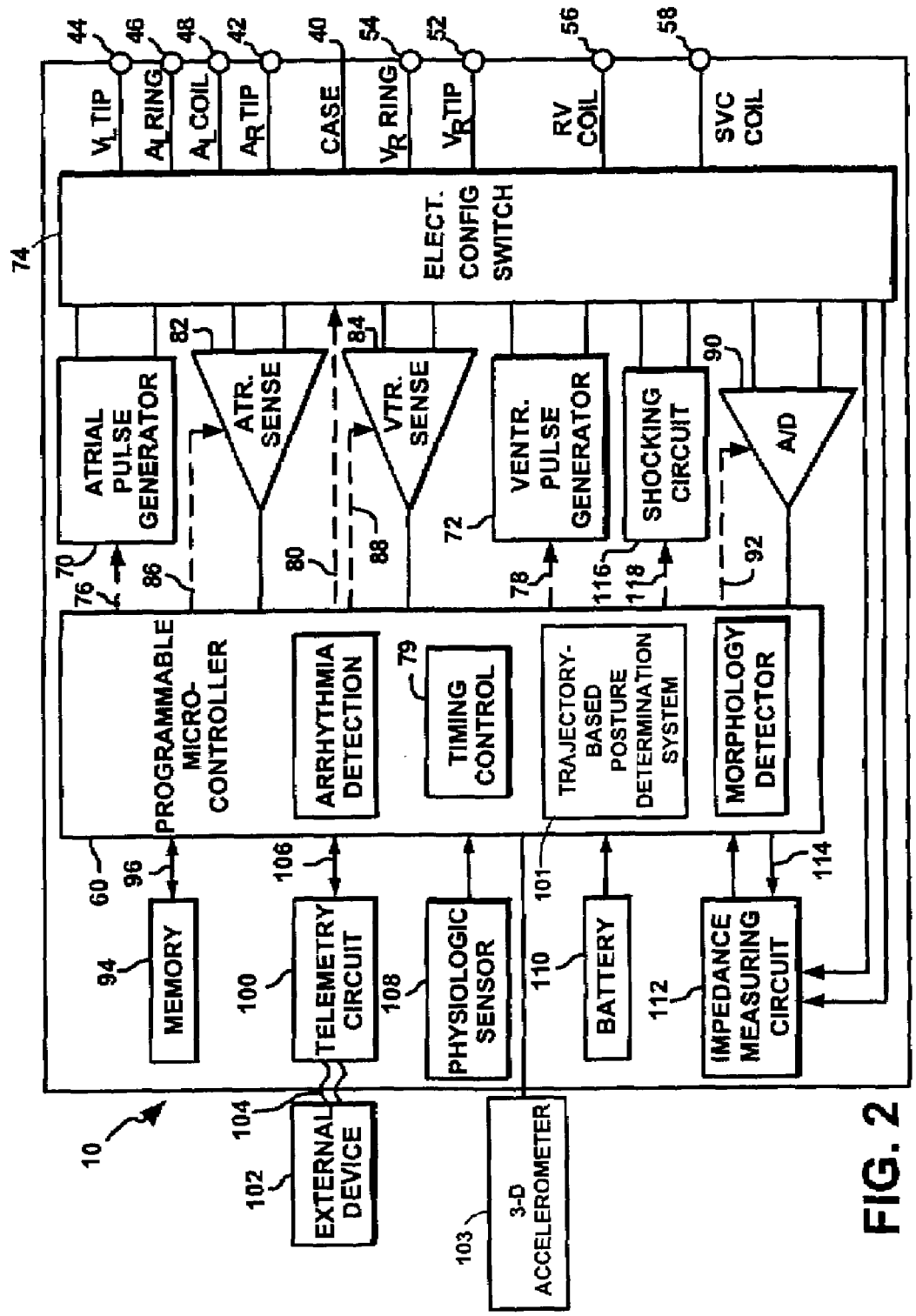
FIG. 2 is a functional block diagram of the multi-chamber implantable stimulation device of FIG. 1 illustrating the basic elements of a stimulation device which can provide cardioversion, defibrillation and pacing stimulation in four chambers of the heart and particularly illustrating a trajectory-based posture determination system.

As illustrated in FIG. 2, a simplified block diagram is shown of the multi-chamber implantable stimulation device 10, which is capable of treating both fast and slow arrhythmias with stimulation therapy, including cardioversion, defibrillation, and pacing stimulation. While a particular multi-chamber device is shown, this is for illustration purposes only, and one of skill in the art could readily duplicate, eliminate or disable the appropriate circuitry in any desired combination to provide a device capable of treating the appropriate chamber(s) with cardioversion, defibrillation and pacing stimulation.

The housing 40 for the stimulation device 10, shown schematically in FIG. 2, is often referred to as the "can", "case" or "case electrode" and may be programmably selected to act as the return electrode for all "unipolar" modes. The housing 40 may further be used as a return electrode alone or in combination with one or more of the coil electrodes, 28, 36 and 38, for shocking purposes. The housing 40 further includes a connector (not shown) having a plurality of terminals, 42, 44, 46, 48, 52, 54, 56, and 58 (shown schematically and, for convenience, the names of the electrodes to which they are connected are shown next to the terminals). As such, to achieve right atrial sensing and pacing, the connector includes at least a right atrial tip terminal ($A_R$ TIP) 42 adapted for connection to the atrial tip electrode 22.

To achieve left chamber sensing, pacing and shocking, the connector includes at least a left ventricular tip terminal ($V_L$ TIP) 44, a left atrial ring terminal ($A_L$ RING) 46, and a left atrial shocking terminal ($A_L$ COIL) 48, which are adapted for connection to the left ventricular ring electrode 26, the left atrial tip electrode 27, and the left atrial coil electrode 28, respectively.

To support right chamber sensing, pacing and shocking, the connector further includes a right ventricular tip terminal ($V_R$ TIP) 52, a right ventricular ring terminal ($V_R$ RING) 54, a right ventricular shocking terminal ($R_V$ COIL) 56, and an SVC shocking terminal (SVC COIL) 58, which are adapted for connection to the right ventricular tip electrode 32, right ventricular ring electrode 34, the RV coil electrode 36, and the SVC coil electrode 38, respectively.

At the core of the stimulation device 10 is a programmable microcontroller 60, which controls the various modes of stimulation therapy. As is well known in the art, the microcontroller 60 typically includes a microprocessor, or equivalent control circuitry, designed specifically for controlling the delivery of stimulation therapy and may further include RAM or ROM memory, logic and timing circuitry, state machine circuitry, and I/O circuitry. Typically, the microcontroller 60 includes the ability to process or monitor input signals (data) as controlled by a program code stored in a designated block of memory. The details of the design and operation of the microcontroller 60 are not critical to the present invention. Rather, any suitable microcontroller 60 may be used that carries out the functions described herein. The use of microprocessor-based control circuits for performing timing and data analysis functions are well known in the art.

As shown in FIG. 2, an atrial pulse generator 70 and a ventricular pulse generator 72 generate pacing stimulation pulses for delivery by the right atrial lead 20, the right ventricular lead 30, and/or the coronary sinus lead 24 via an electrode configuration switch 74. It is understood that in order to provide stimulation therapy in each of the four chambers of the heart, the atrial and ventricular pulse generators, 70 and 72, may include dedicated, independent pulse generators, multiplexed pulse generators, or shared pulse generators. The pulse generators, 70 and 72, are controlled by the microcontroller 60 via appropriate control signals, 76 and 78, respectively, to trigger or inhibit the stimulation pulses.

The microcontroller 60 further includes timing control circuitry 79 which is used to control the timing of such stimulation pulses (e.g., pacing rate, atrio-ventricular (AV) delay, atrial interconduction (A—A) delay, or ventricular interconduction (V—V) delay, etc.) evoked response windows, alert intervals, marker channel timing, etc., which is well known in the art.

The switch 74 includes a plurality of switches for connecting the desired electrodes to the appropriate I/O circuits, thereby providing complete electrode programmability. Accordingly, the switch 74, in response to a control signal 80 from the microcontroller 60, determines the polarity of the stimulation pulses (e.g., unipolar, bipolar, combipolar, etc.) by selectively closing the appropriate combination of switches (not shown) as is known in the art.

Atrial sensing circuits 82 and ventricular sensing circuits 84 may also be selectively coupled to sense voltages between any of the electrodes of the right atrial lead 20, coronary sinus lead 24, and the right ventricular lead 30, and the can, through the switch 74 for sensing the presence of cardiac activity in each of the four chambers of the heart. Accordingly, the atrial (ATR. SENSE) and ventricular (VTR. SENSE) sensing circuits, 82 and 84, may include dedicated sense amplifiers, multiplexed amplifiers, or shared amplifiers. The switch 74 determines the "sensing polarity" of the cardiac signal by selectively closing the appropriate switches, as is also known in the art. In this way, the clinician may program the sensing polarity independent of the stimulation polarity.

Each sensing circuit, 82 and 84, preferably employs one or more low power, precision amplifiers with programmable gain and/or automatic gain control, bandpass filtering, and a threshold detection circuit, as known in the art, to selectively sense the cardiac signal of interest. The automatic gain control enables the device 10 to deal effectively with the difficult problem of sensing the low amplitude signal characteristics of atrial or ventricular fibrillation. The outputs of the atrial and ventricular sensing circuits, 82 and 84, are connected to the microcontroller 60 which, in turn, are able to trigger or inhibit the atrial and ventricular pulse generators, 70 and 72, respectively, in a demand fashion in response to the absence or presence of cardiac activity in the appropriate chambers of the heart. The sensing circuits, 82 and 84, in turn, receive control signals over signal lines, 86 and 88, from the microcontroller 60 for purposes of controlling the gain, threshold, polarization charge removal circuitry (not shown), as is known in the art.

For arrhythmia detection, the device 10 senses cardiac signals to determine whether a rhythm is physiologic or pathologic. As used herein "sensing" is reserved for the noting of an electrical signal, and "detection" is the processing of these sensed signals and noting the presence of an arrhythmia. The timing intervals between sensed events (e.g., P-waves, R-waves, and depolarization signals associated with fibrillation which are sometimes referred to as "F-waves" or "Fib-waves") are then classified by the microcontroller 60 by comparing them to a predefined rate zone limit (i.e., bradycardia, normal, low rate VT, high rate VT, and fibrillation rate zones) and various other characteristics (e.g., sudden onset, stability, physiologic sensors, and morphology, etc.) in order to determine the type of remedial therapy that is needed (e.g., bradycardia pacing, anti-tachycardia pacing, cardioversion shocks or defibrillation shocks, collectively referred to as "tiered therapy").

Cardiac signals are also applied to the inputs of an analog-to-digital (A/D) data acquisition system 90. The data acquisition system 90 is configured to acquire intracardiac electrogram signals, convert the raw analog data into a digital signal, and store the digital signals for later processing and/or telemetric transmission to an external device 102. The data acquisition system 90 is coupled to the right atrial lead 20, the coronary sinus lead 24, and the right ventricular lead 30 through the switch 74 to sample cardiac signals across any pair of desired electrodes.

The microcontroller 60 is further coupled to a memory 94 by a suitable data/address bus 96, wherein the programmable operating parameters used by the microcontroller 60 are stored and modified, as required, in order to customize the operation of the stimulation device 10 to suit the needs of a particular patient. Such operating parameters define, for example, pacing pulse amplitude, pulse duration, electrode polarity, rate, sensitivity, automatic features, arrhythmia detection criteria, and the amplitude, waveshape and vector of each shocking pulse to be delivered to the patient's heart 12 within each respective tier of therapy.

Advantageously, the operating parameters of the implantable device 10 may be non-invasively programmed into the memory 94 through a telemetry circuit 100 in telemetric communication with the external device 102, such as a programmer, transtelephonic transceiver, or a diagnostic system analyzer. The telemetry circuit 100 is activated by the microcontroller by a control signal 106. The telemetry circuit 100 advantageously allows intracardiac electrograms and status information relating to the operation of the device 10 (as contained in the microcontroller 60 or memory 94) to be sent to the external device 102 through an established communication link 104.

Microcontroller 60 also includes a trajectory-based posture determination system 101, which operates to detect patient posture in accordance with a technique described in detail below primarily with reference to FIGS. 4–9. The posture determination system determines posture or changes in posture based on signals received from a three-axis accelerometer 103, which may be external to device can 10 (as shown) or internal to the can or may include multiple separate accelerometers mounted at different locations. The accelerometer may be, for example, a MEMS (micro-electromechanical system) 3-D accelerometer of the type exploiting capacitive or optical cantilever beam techniques. The detection of posture or changes in posture is used to control operations of the implanted device such as to selectively control pacing rate or to enable or inhibit cardioversion or shocking functions. In this regard, the posture determination system may be used alone or in combination with a physiologic sensor 108, commonly referred to as a "rate-responsive" sensor because it is typically used to adjust pacing stimulation rate according to the exercise state of the patient. However, the physiological sensor 108 may further be used to detect changes in cardiac output, changes in the physiological condition of the heart, or diurnal changes in activity (e.g., detecting sleep and wake states). Accordingly, the microcontroller 60 responds by adjusting the various pacing parameters (such as rate, AV Delay, V—V Delay, etc.) at which the atrial and ventricular pulse generators, 70 and 72, generate stimulation pulses.

In addition, the stimulation device may be configured to perform Automatic Mode Switching (AMS) wherein the pacemaker reverts from a tracking mode such as a VDD or DDD mode to a nontracking mode such as VVI or DDI mode. VDD, DDD, VVI and DDI are standard device codes that identify the mode of operation of the device. DDD indicates a device that senses and paces in both the atria and the ventricles and is capable of both triggering and inhibiting functions based upon events sensed in the atria and the ventricles. VDD indicates a device that sensed in both chambers but only paces in the ventricle. A sensed event on the atrial channel triggers a ventricular output after a programmable delay, the pacemaker's equivalent of a PR interval. VVI indicates that the device is capable of pacing and sensing only in the ventricles and is only capable of inhibiting the functions based upon events sensed in the ventricles. DDI is identical to DDD except that the device is only capable of inhibiting functions based upon sensed events, rather than triggering functions. As such, the DDI mode is a non-tracking mode precluding its triggering ventricular outputs in response to sensed atrial events. Numerous other device modes of operation are possible, each represented by standard abbreviations of this type.

The stimulation device additionally includes a battery 110, which provides operating power to all of the circuits shown in FIG. 2. For the stimulation device 10, which employs shocking therapy, the battery 110 must be capable of operating at low current drains for long periods of time, and then be capable of providing high-current pulses (for capacitor charging) when the patient requires a shock pulse. The battery 110 must also have a predictable discharge characteristic so that elective replacement time can be detected. Accordingly, the device 10 preferably employs lithium/silver vanadium oxide batteries, as is true for most (if not all) current devices.

As further shown in FIG. 2, the device 10 is shown as having an impedance measuring circuit 112 which is enabled by the microcontroller 60 via a control signal 114. The impedance measuring circuit 112 is not critical to the present invention and is shown for only completeness.

In the case where the stimulation device 10 is intended to operate as an implantable cardioverter/defibrillator (ICD) device, it must detect the occurrence of an arrhythmia, and automatically apply an appropriate electrical shock therapy to the heart aimed at terminating the detected arrhythmia. To this end, the microcontroller 60 further controls a shocking circuit 116 by way of a control signal 118. The shocking circuit 116 generates shocking pulses of low (up to 0.5 joules), moderate (0.5–10 joules), or high energy (11 to 40 joules), as controlled by the microcontroller 60. Such shocking pulses are applied to the patient's heart 12 through at least two shocking electrodes, and as shown in this embodiment, selected from the left atrial coil electrode 28, the RV coil electrode 36, and/or the SVC coil electrode 38. As noted above, the housing 40 may act as an active electrode in combination with the RV electrode 36, or as part of a split electrical vector using the SVC coil electrode 38 or the left atrial coil electrode 28 (i.e., using the RV electrode as a common electrode).

Cardioversion shocks are generally considered to be of low to moderate energy level (so as to minimize pain felt by the patient), and/or synchronized with an R-wave and/or pertaining to the treatment of tachycardia. Defibrillation shocks are generally of moderate to high energy level (i.e., corresponding to thresholds in the range of 5–40 joules), delivered asynchronously (since R-waves may be too disorganized), and pertaining exclusively to the treatment of fibrillation. Accordingly, the microcontroller 60 is capable of controlling the synchronous or asynchronous delivery of the shocking pulses.

Device Programmer Overview

Figure 3:
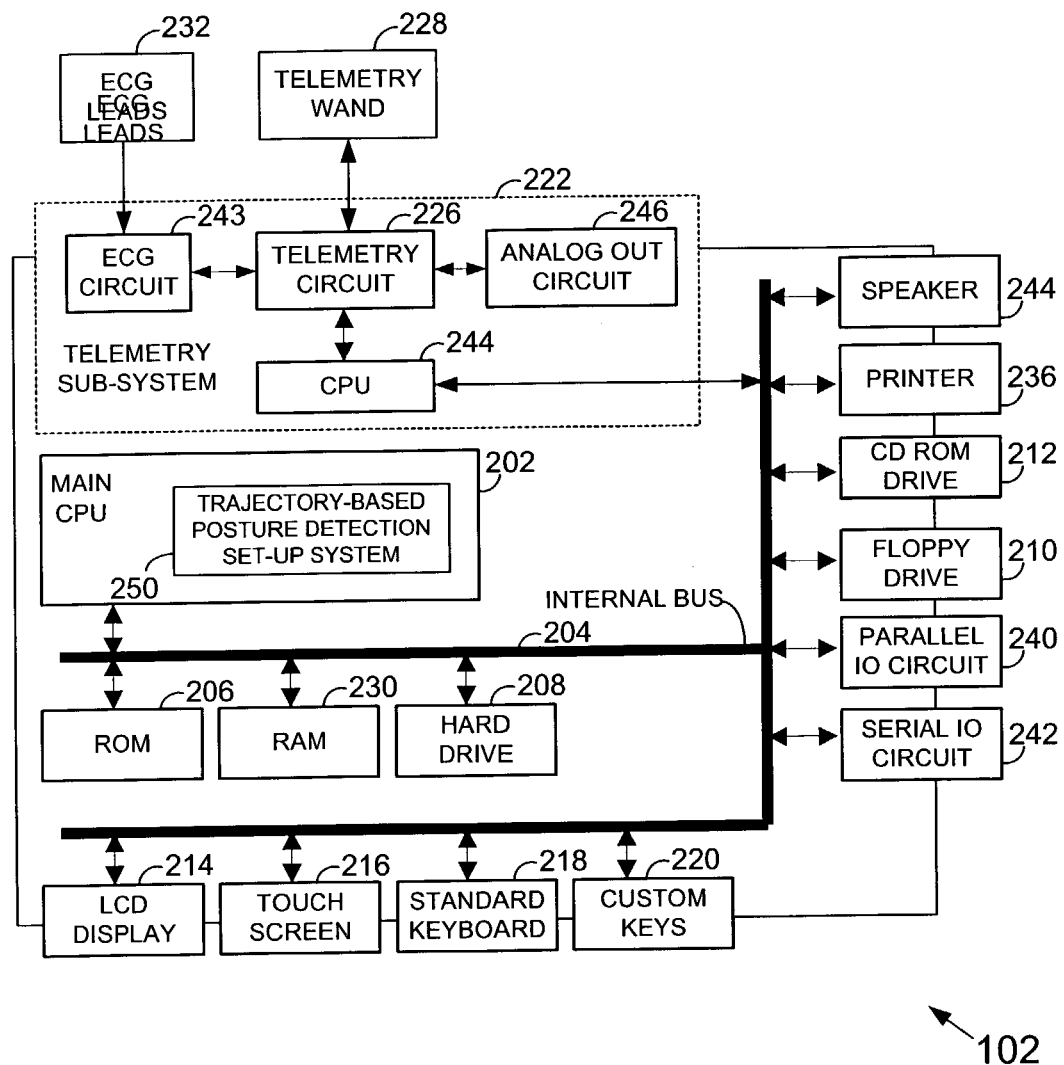
FIG. 3 is a functional block diagram illustrating components of a programmer for use in programming the implantable device of FIG. 1, and in particular illustrating a change in posture determination set-up system for use in programming the posture determination system of the implantable device.

FIG. 3 illustrates pertinent components of an external programmer for use in programming an implantable medical device such as a pacemaker or ICD. Briefly, the programmer permits a physician or other user to program the operation of the implanted device and to retrieve and display information received from the implanted device such as IEGM data and device diagnostic data. Additionally, the external programmer receives and displays ECG data from separate external ECG leads that may be attached to the patient. Depending upon the specific programming of the external programmer, programmer 102 may also be capable of processing and analyzing data received from the implanted device and from the ECG leads to, for example, render preliminary diagnosis as to medical conditions of the patient or to the operations of the implanted device.

Now, considering the components of programmer 102, operations of the programmer are controlled by a CPU 202, which may be a generally programmable microprocessor or microcontroller or may be a dedicated processing device such as an application specific integrated circuit (ASIC) or the like. Software instructions to be performed by the CPU are accessed via an internal bus 204 from a read only memory (ROM) 206 and random access memory 230. Additional software may be accessed from a hard drive 208, floppy drive 210, and CD ROM drive 212, or other suitable permanent mass storage device. Depending upon the specific implementation, a basic input output system (BIOS) is retrieved from the ROM by CPU at power up. Based upon instructions provided in the BIOS, the CPU "boots up" the overall system in accordance with well-established computer processing techniques.

Once operating, the CPU displays a menu of programming options to the user via an LCD display 214 or other suitable computer display device. To this end, the CPU may, for example, display a menu of specific programming parameters of the implanted device to be programmed or may display a menu of types of diagnostic data to be retrieved and displayed. In response thereto, the physician enters various commands via either a touch screen 216 overlaid on the LCD display or through a standard keyboard 218 supplemented by additional custom keys 220, such as an emergency WI (EVVI) key. The EVVI key sets the implanted device to a safe VVI mode with high pacing outputs. This ensures life sustaining pacing operation in nearly all situations but by no means is it desirable to leave the implantable device in the EWI mode at all times.

Typically, the physician initially controls the programmer 102 to retrieve data stored within the implanted medical device and to also retrieve ECG data from ECG leads, if any, coupled to the patient. To this end, CPU 202 transmits appropriate signals to a telemetry subsystem 222, which provides components for directly interfacing with the implanted device, and the ECG leads. Telemetry subsystem 222 includes its own separate CPU 224 for coordinating the operations of the telemetry subsystem. Main CPU 202 of programmer communicates with telemetry subsystem CPU 224 via internal bus 204. Telemetry subsystem additionally includes a telemetry circuit 226 connected to a telemetry wand 228, which, in turn, receives and transmits signals electromagnetically from a telemetry unit of the implanted device. The telemetry wand is placed over the chest of the patient near the implanted device to permit reliable transmission of data between the telemetry wand and the implanted device. Typically, at the beginning of the programming session, the external programming device controls the implanted device via appropriate signals generated by the telemetry wand to output all previously recorded patient and device diagnostic information. Patient diagnostic information includes, for example, recorded IEGM data and statistical patient data such as the percentage of paced versus sensed heartbeats. Device diagnostic data includes, for example, information representative of the operation of the implanted device such as lead impedances, battery voltages, battery recommended replacement time (RRT) information and the like. Data retrieved from the implanted device is stored by external programmer 102 either within a random access memory (RAM) 230, hard drive 208 or within a floppy diskette placed within floppy drive 210. Additionally, or in the alternative, data may be permanently or semi-permanently stored within a compact disk (CD) or other digital media disk, if the overall system is configured with a drive for recording data onto digital media disks, such as a write once read many (WORM) drive.

Once all patient and device diagnostic data previously stored within the implanted device is transferred to programmer 102, the implanted device may be further controlled to transmit additional data in real time as it is detected by the implanted device, such as additional IEGM data, lead impedance data, and the like. Additionally, or in the alternative, telemetry subsystem 222 receives ECG signals from ECG leads 232 via an ECG processing circuit 234. As with data retrieved from the implanted device itself, signals received from the ECG leads are stored within one or more of the storage devices of the external programmer. Typically, ECG leads output analog electrical signals representative of the ECG. Accordingly, ECG circuit 234 includes analog to digital conversion circuitry for converting the signals to digital data appropriate for further processing within programmer. Depending upon the implementation, the ECG circuit may be configured to convert the analog signals into event record data for ease of processing along with the event record data retrieved from the implanted device. Typically, signals received from the ECG leads are received and processed in real time.

Thus, the programmer receives data both from the implanted device and from the external ECG leads. Data retrieved from the implanted device includes parameters representative of the current programming state of the implanted device. Under the control of the physician, the external programmer displays the current programming parameters and permits the physician to reprogram the parameters. To this end, the physician enters appropriate commands via any of the aforementioned input devices and, under control of CPU 202, the programming commands are converted to specific programming parameters for transmission to the implanted device via telemetry wand 228 to thereby reprogram the implanted device. Prior to reprogramming specific parameters, the physician may control the external programmer to display any or all of the data retrieved from the implanted device or from the ECG leads, including displays of ECGs, IEGMs, and statistical patient information. Any or all of the information displayed by programmer may also be printed using a printer 236.

CPU 202 includes a posture determination set-up system 250 for generating information for transmission to the posture determination system of the implanted device of FIG. 3, which the posture determination system then uses to facilitate posture determination. The operation of set-up system 250 is described in detail below primarily with reference to FIG. 10.

Programmer 102 also includes a modem 238 to permit direct transmission of data to other programmers via the public switched telephone network (PSTN) or other interconnection line, such as a T1 line or fiber optic cable. Depending upon the implementation, the modem may be connected directly to internal bus 204 may be connected to the internal bus via either a parallel port 240 or a serial port 242. Other peripheral devices may be connected to the external programmer via parallel port 240 or a serial port 242 as well. Although one of each is shown, a plurality of input output (IO) ports might be provided.

A speaker 244 is included for providing audible tones to the user, such as a warning beep in the event improper input is provided by the physician. Telemetry subsystem 222 additionally includes an analog output circuit 246 for controlling the transmission of analog output signals, such as IEGM signals output to an ECG machine or chart recorder.

With the programmer configured as shown, a physician or other user operating the external programmer is capable of retrieving, processing and displaying a wide range of information received from the ECG leads or from the implanted device and to reprogram the implanted device if needed. The descriptions provided herein with respect to FIG. 3 are intended merely to provide an overview of the operation of programmer and are not intended to describe in detail each and every feature of the hardware and software of the device and is not intended to provide an exhaustive list of the functions performed by the device.

In the remaining figures, flow charts are provided for illustrating the operation and novel features of various exemplary embodiments of the invention. In the flow chart, various algorithmic steps are summarized in individual "blocks". Such blocks describe specific actions or decisions to be made or carried out as the algorithm proceeds. Where a microcontroller (or equivalent) is employed, the flow charts presented herein provide the basis for a "control program" that may be used by such a microcontroller (or equivalent) to effectuate the desired control of the device. Those skilled in the art may readily write such a control program based on the flow charts and other descriptions presented herein.

Detection of Selected Patient Posture

Figure 4:
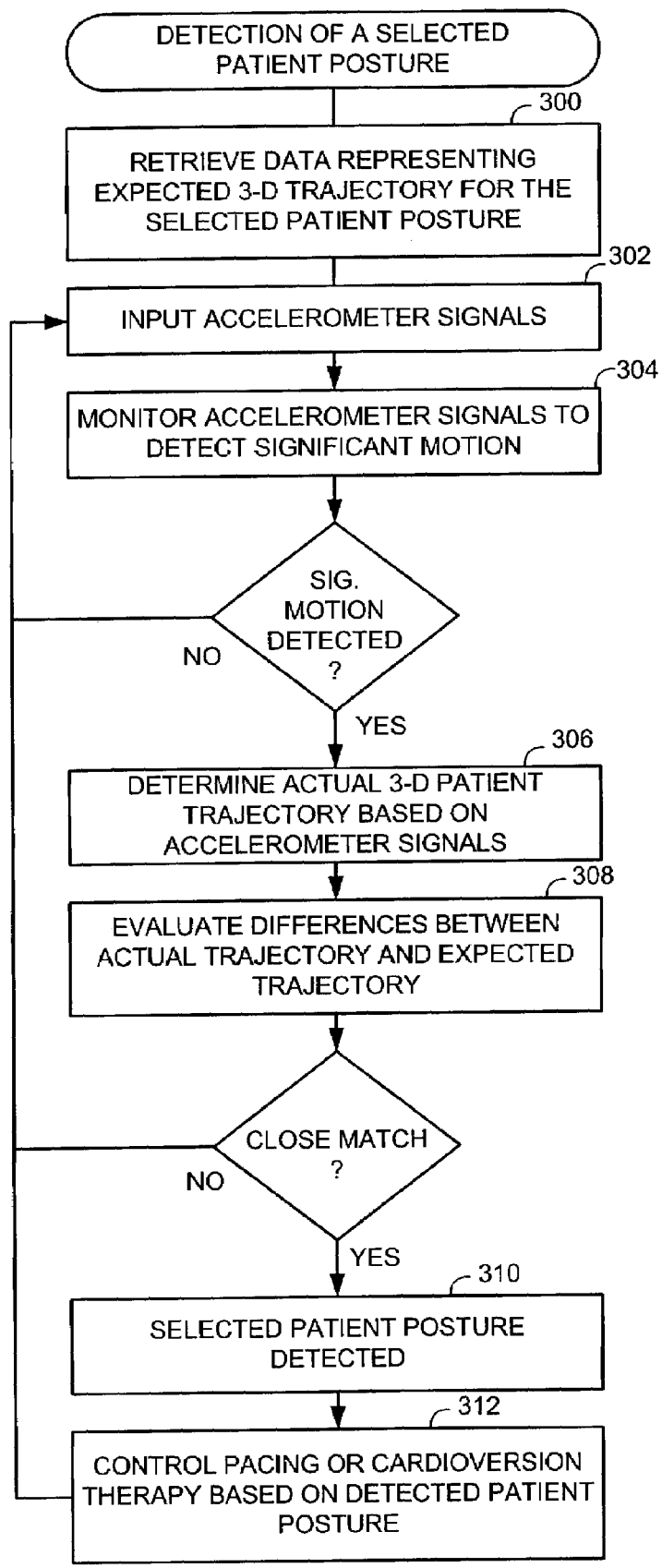
FIG. 4 is a flow chart providing an overview of a first exemplary technique performed by the change in posture determination of FIG. 2, particularly directed toward detecting the occurrence of a particular posture or change in posture based on a 3D spatial trajectory of the patient.

FIG. 4 provides an overview of an individual patient posture detection technique performed by posture detection system 101 of FIG. 2. The technique operates to detect one selected patient posture, which may be a static posture, dynamic posture or change in posture. A more general technique for discriminating among many possible patient postures is described below with reference to FIGS. 8 and 9. The simpler technique of FIG. 4 is most useful for applications wherein there is only one particular patient posture of interest and wherein, perhaps as a result of resource imitations within the implantable device, implementation of the more general technique may not be feasible. An example of an application wherein only one particular posture may need to be detected is an implantable warning device intended to merely detect whether a patient has fallen, perhaps for the purposes of transmitting warning signals to supervisory personnel. However, any of a variety of patient postures may be detected in principle. A partial list of patient postures that may be selected for use with the technique is provided in TABLE I. This list is by no means exhaustive.

TABLE I

| PATIENT POSTURES | | |
|---|---|---|
| STATIC POSTURES | DYNAMIC POSTURES | CHANGES IN POSTURE |
| Sitting | Walking On A Level Surface | Sitting To Standing |
| Standing | Walking Up Stairs | Standing To Sitting |
| Lying prone | Walking Down Stairs | Rising From A Prone Position |
|  | Running | Reclining To A Prone Position |
|  | Pedaling | Rolling Over While In A Prone Position |
|  |  | Sudden Falling |

Initially, at step 300, the device retrieves data representing the 3-D trajectory expected to be associated with the particular patient posture to be detected. In the case of a change in posture, the retrieved trajectory represents the movement of the chest of the patient expected to occur as the patient switches from one posture to another such as while the patient rises from a seated position to a standing position. In the case of dynamic posture, the retrieved trajectory represents the movement of the chest expected to occur as the patient maintains the dynamic posture such as while the patient walks up stairs. In the case of a static posture, the posture detection system first detects the change in posture leading to the static posture to be detected. So to detect whether the patient is sitting, the system first detects the change in posture associated with standing to sitting and hence retrieves the trajectory associated therewith.

At step 302, the device inputs accelerometer signals from the three-axis accelerometer (item 103 of FIG. 2). The accelerometer signals are orthogonal signals representative of the acceleration of the accelerometer in three mutually perpendicular directions. More specifically, the accelerometer is preferably oriented to provide a first acceleration signal $a_x(t)$ along a lateral-medial (L-M) axis, a second acceleration signal $a_y(t)$ along an superior-inferior (S-I) axis, and a third acceleration signal $a_z(t)$ along a anterior-posterior (A-P) axis within the chest cavity of the patient. Each acceleration signal varies continuously with time as a result of any motion of the patient. The acceleration signals are initially received as analog signals, which are then sampled at a frequency of, for example, one millisecond to provide digitized versions of the acceleration signals.

At step 304, the device monitors the acceleration signals to detect any significant new motion, i.e. motion significant enough to be consistent with a dynamic posture or a change in posture. In this regard, otherwise conventional activity signal-based techniques may be utilized to monitor the acceleration signals and to compare those signals against a predetermined threshold representative of a change in posture. So long as the acceleration signals do not indicate any significant motion, steps 302 and 304 are repeated in a loop. However, once significant motion is detected, the device, at step 306, determines the actual 3-D trajectory of the chest of the patient based upon the accelerometer signals. The 3-D trajectory may be derived from the accelerometer signals by integrating the acceleration signals to produce orthogonal position time-series signals $p_x(t)$, $p_y(t)$, and $p_z(t)$. In other words, the device effectively calculates:

$$P_x(t) = \int \int a_x(t) dt\, dt;$$

$$P_y(t) = \int \int a_y(t) dt\, dt;$$

$$P_z(t) = \int \int a_z(t) dt\, dt.$$

However, since the device processes discrete, digitized acceleration values rather than continuous acceleration functions, it performs corresponding summation operations to derive the position values from the acceleration values. A suitable algorithm for performing the summation is as follows:

```
For D=x,y,z
  PTemp=0
  V=0
  For J=1:T
    For I=1:TA
      V=V+a_D(I)*d
    End
    PTemp=PTemp+V*(TA*d)
    P_D(J)=PTemp
  End
End
```

In the foregoing, V represents velocity, P represents positional distance, TA is number of sample points provided by the accelerometer, T is the number of position data points to be generated, and the sampling interval is represented by d. When the number of values output from accelerometer (TA) exceeds a predetermined threshold, the pacemaker may be configured to store the accelerometer output into a buffer. TA is equal to the data acquisition time divided by the sampling interval. TA may be in the range of, for example, 20 to 100 values for a typical change in posture. In one example, where ten acceleration samples are generated per second and where the change in posture takes five seconds, TA is about 50. T may be set to a different value than TA and may also be in the range of, for example, 20 to 100 values. Preferably, T is set to be equal the number of rows in the pre-calculated Z matrix described below, so as to facilitate computational efficiency.

At step 308, the device compares the actual 3-D trajectory of the chest of the patient determined at step 306 with the expected 3-D trajectory retrieved at step 300 to evaluate any differences therebetween. That is, the device determines how closely to the actual trajectory matches the expected trajectory and, if there is a close match, the device to thereby concludes, at step 310, that the particular dynamic posture is ongoing or that the change in posture has just occurred. At step 312, the device then controls its functions in response to the detected change in posture. For example, if the device is programmed to detect whenever the patient stands up, the pacemaker may then temporarily increase the pacing rate at step 312 to ensure adequate blood flow within the patient to thereby reduce the risk of dizziness or fainting. As another sample, if the device has been programmed to detect when a patient is walking up stairs, the device may then inhibit at step 312 delivery of cardioversion shocks that might otherwise be delivered until the patient is no longer deemed to be walking up or down stairs. (This assumes, of course, that an arrhythmia requiring a cardioversion shock, such as atrial fibrillation, has been simultaneously detected by other components of the device.) These are simply a few examples of how functions of an implantable medical device may be controlled based upon a detection of patient posture and is not meant to be exhaustive. In any case, once any changes have been made to the functions performed by the implanted device, processing returns to step 302 for detecting additional accelerometer signals for purposes of detecting a next occurrence of the selected patient posture.

Figure 5:
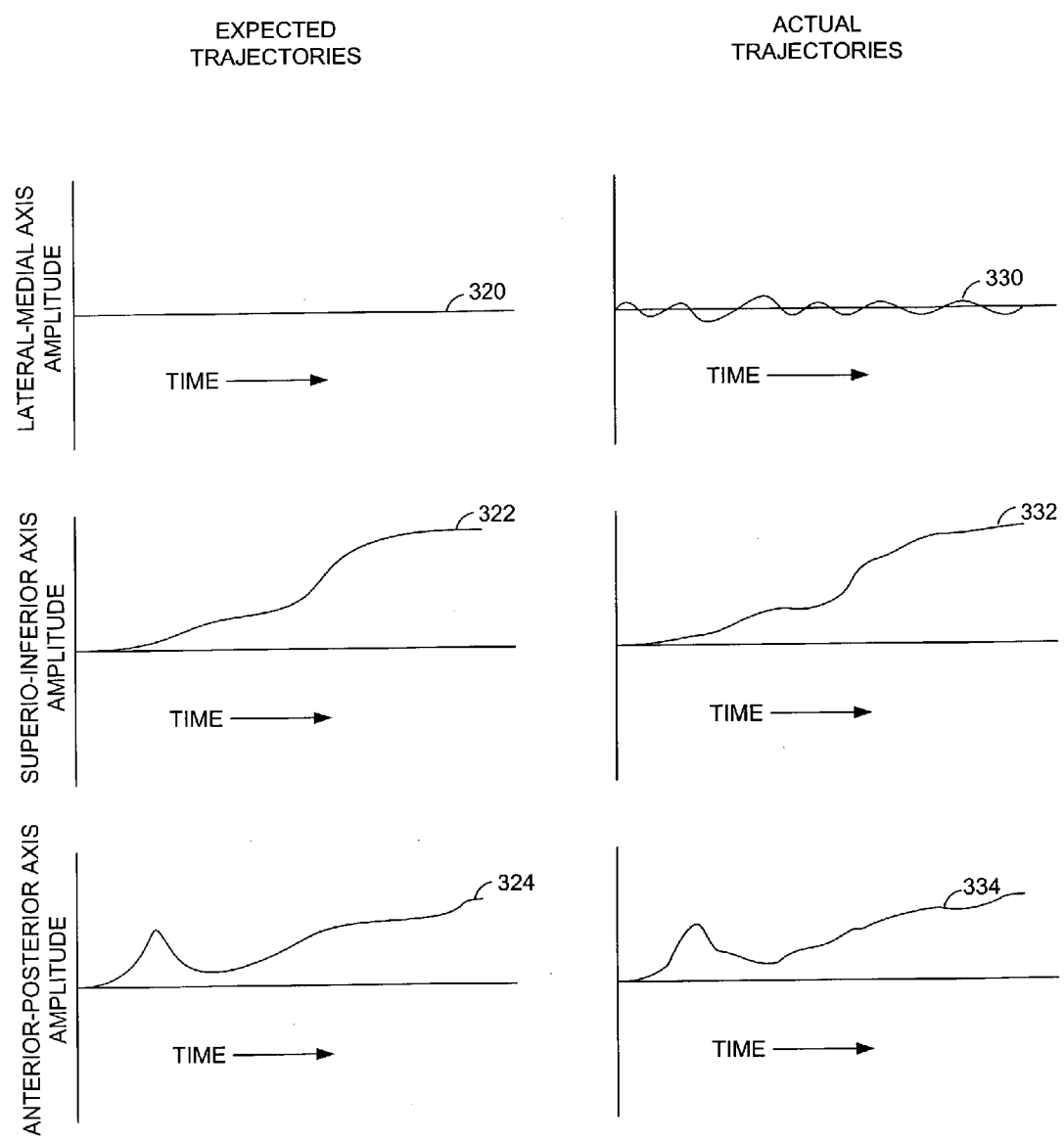
FIG. 5 is a graphic representation of an exemplary 3-D trajectory of a patient detected during a change in posture and an exemplary 3-D trajectory expected to occur while rising from a seated position to a standing position for use with the method of FIG. 4.

Thus, the technique of FIG. 4 operates to compare actual 3-D patient trajectories with the trajectory expected to occur during a particular change in posture or during an on-going dynamic posture. Exemplary expected 3-D patient trajectories and actual trajectories are shown in FIG. 5 for a change in posture of rising from a seated position to a standing position. Graphs 320, 322, and 324 are provided showing the expected magnitude of the motion (in arbitrary units) of an accelerometer implanted within the chest of the patient along each of the three orthogonal axes as a function of time. More specifically, graph 320 illustrates the expected motion along the lateral-medial axis of the accelerometer, i.e. it illustrates motion of the chest perpendicular to the direction the patient is moving. Although the chest of a person is likely to wobble slightly to the left or right during the change in posture, on the average such wobbling will be substantially random and hence graph 320 shows no average motion. Graph 322 illustrates the expected motion along the superior-inferior axis of the accelerometer, i.e. it illustrates the expected upward movement of the chest, which is significant. Graph 324 illustrates the expected motion along the anterior-posterior axis of the accelerometer, i.e. it illustrates the expected forward movement of the chest, which is also significant. As can be seen, the chest is expected to initially move forward fairly sharply (as shown in graph 324), then move backward, before again moving forward as the person finally rises and straightens to a standing position. This is a result of an expected initial forward tilt of the chest occurring prior to straightening out. Note that, during this initial tilting phase, the elevation of the chest (as shown in graph 322) is not expected to increase by much.

The exemplary actual 3-D trajectory signals, generated at step 306 of FIG. 4, are illustrated in FIG. 5 with graphs 330, 332, and 334, which represent, respectively, motion along the lateral-medial, superior-inferior, and anterior-posterior axes of the accelerometer. Graphs 330, 332 and 334 represent actual patient movement and hence appear, as shown in FIG. 5, as relatively rough, "noisy" graphs. Graph 330, in particular, shows some wobble occurring along the lateral-medial while the patient rises. As can be seen by the trajectory of graphs 330, 332, and 334, the actual motion along each of the three axes matches the expected motion fairly closely and so the conclusion is drawn at step 310, that the patient has just stood up. Any other variety of techniques may be employed to determine whether the actual trajectories match the expected trajectories. For example, a template representative of the expected trajectory as a function of time may be stored in the memory of the device, then the actual trajectory is compared against the template to generate a numerical metric or value representative of the total difference between the two. If this metric falls below a predetermined threshold, then a conclusion is drawn that the two trajectories matched sufficiently. In this regard, a wide variety of otherwise conventional comparison techniques may be employed and such techniques will not be described in detail herein. However, a more sophisticated technique for making the comparison, which is based upon the use of pre-calculated comparison matrices is described in detail with reference to FIG. 6.

Although the technique of FIG. 4 has been described with reference to an example wherein the device waits until the change in posture has been completed before detecting the change in posture, this is not necessarily required. Depending upon the particular change posture, in many cases it is feasible to detect the change in posture while it is occurring. In the example of FIG. 5, for example, it is possible to detect that the patient is in the act of standing up based upon only the first half of the actual and expected trajectories illustrated in the graphs. Hence, the functions of the device may be adjusted or modified during the change in posture, rather than only following completion of the change in posture. For example, as the patient is in the process of standing up, the device may detect the ongoing change in posture and immediately increase the pacing rate. Moreover, for detection of on-going dynamic postures such as running or pedaling, posture detection occurs once the system has evaluated enough of the patient trajectory to make a reliable determination of the patient posture. Preferably, the technique is implemented to compare only as much of the actual trajectory against the expected trajectory to make a reliable detection. The amount of data that needs to be compared depends upon the particular patient posture under consideration and other factors such as, for example, the amount of noise in the data. Routine experimentation may be used to be determined how much data is required to ensure reliable detection of patient posture.

Figure 6:
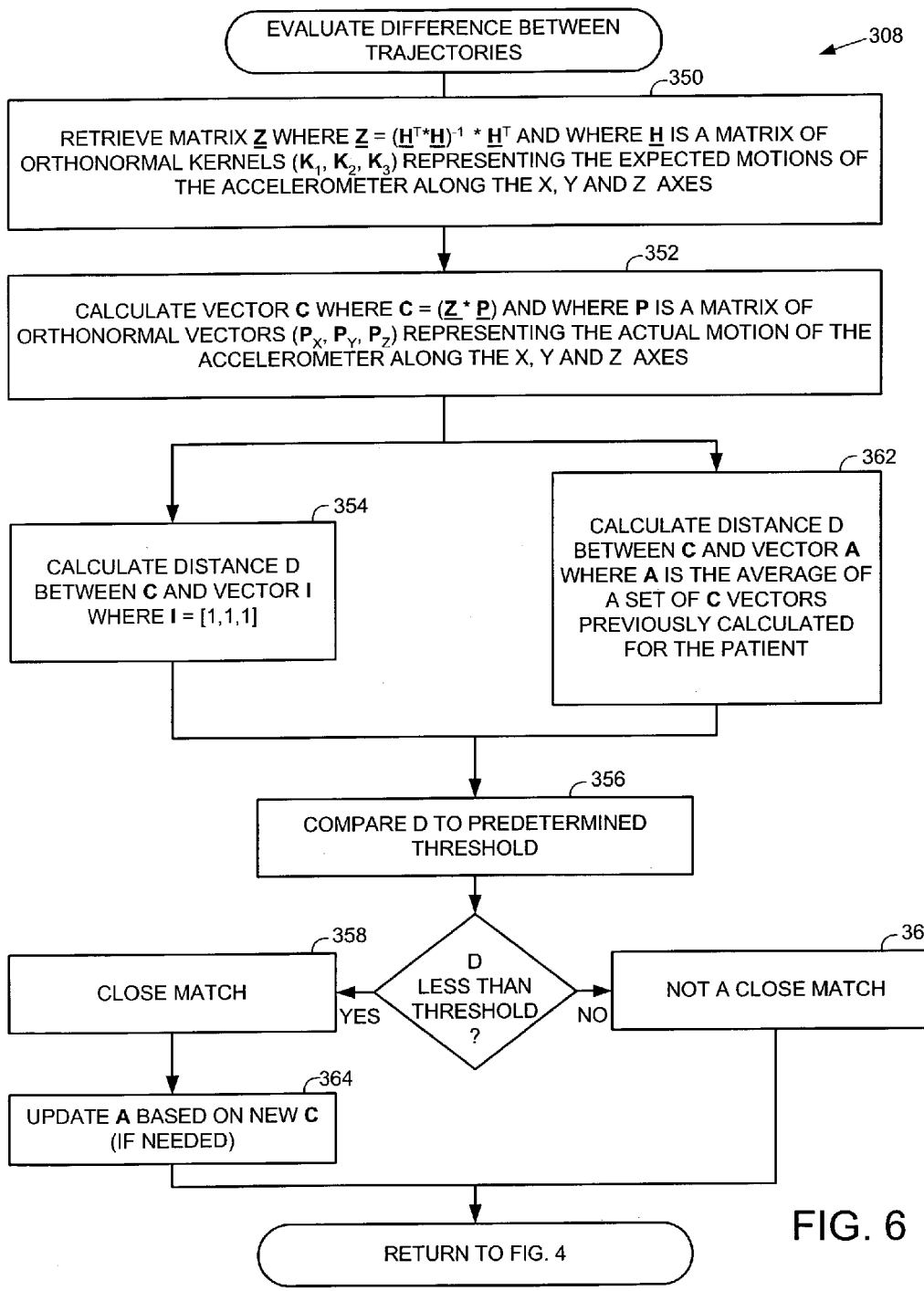
FIG. 6 is a flow chart illustrating, in detail, an evaluation method performed as part of the technique of FIG. 4 for evaluating the degree of difference between the actual 3D trajectory of the patient and the expected 3D trajectory for the posture or change in posture to be detected based, in part, on a single pre-calculated comparison matrix Z.

Referring now to FIG. 6, a matrix-based technique for evaluating the difference between an actual patient trajectory and the expected trajectory (at step 308 of FIG. 4) will now be described in detail. FIG. 6 will be described with reference to an example wherein a change is posture is to be detected but the technique is also applicable to detection of an on-going dynamic posture. The matrix-based technique has the advantage of providing for a reliable comparison between the actual and expected trajectories while consuming relatively modest memory and processing resources within the implantable device. In particular, the technique permits certain matrices to be pre-calculated within an external programmer (FIG. 3) for subsequent use within the implantable device to reduce the processing burden on the microcontroller of the implantable device. Moreover, the matrices are generated in a relatively compact form to reduce memory requirements within the implanted device. Techniques for pre-calculating the various matrices are described in greater detail with reference to FIG. 10.

More specifically, the technique of FIG. 6 be essentially operates to solve the matrix equation P=H*C for C wherein P is a matrix of time-series values representing the actual trajectory of the patient, wherein H is a matrix of time-series values representing the expected trajectory of the patient (derived, for example, from a population of patients), and wherein C is a correction vector representing an any differences between the actual trajectory and the expected to directory. Accordingly, the closer that C is to the identity matrix I wherein I=[1,1,1], the closer the actual trajectory is to the expected trajectory. However, rather than requiring the implanted device itself to solve the matrix equation P=H*C for C for each possible change in posture by solving $C=(H^T*H)^{-1}*H^T*P$ (which is a computationally intensive procedure), the value of $(H^T*H)^{-1}*H^T$ is pre-calculated and stored in the implantable device as a comparison matrix Z wherein $Z=(H^T*H)^{-1}*H^T$. Hence, the device need only perform the far less computationally intensive procedure of calculating Z*P to generate the correction vector C. Moreover, rather than representing the expected to trajectory for the patient posture to be detected in terms of actual raw trajectory data stored within matrix H, H is instead initially represented using a set of idealized orthonormal kernels ($K_1$, $K_2$, $K_3$) each representing the expected motion of the accelerometer along one of the orthogonal axes in terms of coefficients to Laguerre functions or Lagrange functions. The use of Laguerre functions or Lagrange functions helps reduce the total amount of data required within matrix H, while still reliably representing the expected trajectory. Hence, when converted to comparison matrix Z, the comparison matrix likewise enjoys a reduction in the total amount of data required. Additionally, by providing for a relatively compact representation of the expected trajectory, the matrix multiplication actually performed by the implant device to calculate correction vector C (i.e. C=Z*P) is likewise simplified. Hence, both memory and processing resources of the implanted device are saved.

P, H, Z, C and I may be represented as follows:

$P=[P_{11}\ P_{21}\ P_{31}$
$\quad P_{12}\ P_{22}\ P_{32}$
$\quad P_{13}\ P_{23}\ P_{33}$
$\quad \ldots$
$\quad \ldots$
$\quad \ldots$
$\quad P_{1T}\ P_{2T}\ P_{3T}]$
$H=[K_{11}\ K_{21}\ K_{31}$
$\quad K_{12}\ K_{22}\ K_{32}$
$\quad K_{13}\ K_{23}\ K_{33}$
$\quad \ldots$
$\quad \ldots$
$\quad \ldots$
$\quad K_{1T}\ K_{2T}\ K_{3T}]$
$C=[C_1\ C_2\ C_3]$
$I=[1\ 1\ 1]$.

As noted above, "T" represents the total number of time-series position values (or position data samples) generated from integrating the accelerometer data. The K coefficients for use in H are derived from the Laguerre functions and the Lagrange functions in accordance with otherwise conventional techniques. See, for example, Marmarelis, V. Z, "Identification of Nonlinear Biological Systems Using Laguerre Expansions of Kernels", Annals of Biomedical Engineering, Vol. 21, pp. 573–589, 1993.

Figure 7:
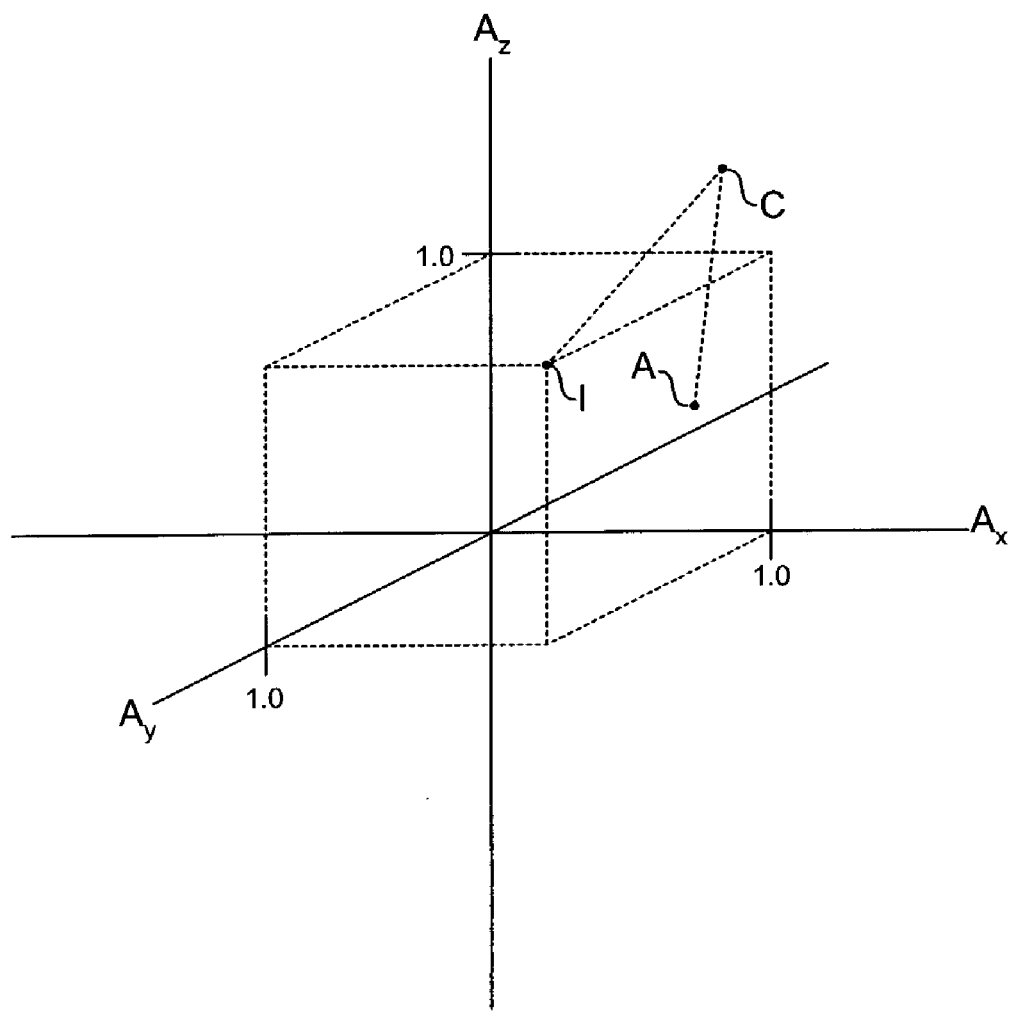
FIG. 7 is a graphic representation of a correction vector C calculated during the evaluation method of FIG. 5 for comparison against either an average correction vector A or an identity vector I.

Initially, at step 350, the device retrieves pre-calculated comparison matrix Z from memory wherein, as noted above, $Z=(H^T*H)^{-1}*H^T$ and H is the matrix of orthonormal kernels ($K_1$, $K_2$, $K_3$) representing the expected motion of the accelerometer along three orthonormal axes during the particular change in posture to be detected. At step 352, the device calculates vector C by performing the matrix multiplication Z*P. The device then determines how closely the actual trajectory (P) matches the expected trajectory (H) by calculating the distance between C and I, at step 354, which is then represented by D. As noted, I=[1,1,1]. Hence, the closer the actual trajectory P is to the expected trajectory H, the closer C will be to I (and recalling that C is equal to $(H^T*H)^{-1}*H^T*P$) and therefore the closer D will be to 0. Thus, the magnitude of D represents the extent to which the actual trajectory matches the expected trajectory for the particular change in posture to be detected. At step 356, D is compared against a pre-determined threshold representative of a close match. If D is less than the threshold, a close match is deemed to have been detected (step 358). Otherwise, no match is deemed to have been detected (step 360). The threshold value is predetermined, in one example, by having the patient, following implant of the device, repeatedly perform the particular change in posture to be detected. Each time the resulting value for D is calculated and stored (either by the implanted device or by an external programmer). In a specific example, the threshold is then set to be equal to the largest of the D values that had been stored. Other techniques can be employed for calculating a suitable value for the threshold. FIG. 7 illustrates an exemplary value for C in comparison with I with the distance between C and I being defined as D.

As an alternative, rather than deriving D by calculating the distance between C and I (at step 354), the device instead derives D by calculating the distance between C and an average vector A, at step 362. A is the average of a set of previously calculated C vectors determined for the patient while repeatedly undergoing the change in posture to be detected. In one example, following implant of the device, the patient is instructed repeatedly perform the particular change in posture of interest. The device (or an external programmer) then calculates and stores a vector C for each repetition of the change in posture, resulting in a cluster of C vectors. A is then derived by determining the centroid of the cluster of stored C vectors and is stored in the implanted device. In any case, the closer C is to A, the closer D is to 0, and the more likely the current change in posture matches the particular change in posture to be detected. Again, at step 356, D is compared against a pre-determined threshold representative of a close match. Note, though, that the threshold used for comparison against the D calculated at step 362 may differ from the threshold used from comprising against the D derived at step 354, but may be pre-calculated using similar techniques.

FIG. 7 also illustrates an exemplary value for A. With this latter technique, A essentially represents the average correction for the particular patient between the expected trajectory H (derived from a population of patients and represented in terms of orthonormal kernels) and the actual trajectory. For many patients, A is fairly close to [1,1,1]. However, for other patients, perhaps as a result of significant idiosyncrasies in the specific manner of making the given change in posture, their typical trajectory during the change in posture will differ from the expected trajectory as derived from the population. Hence, for those patients, A may differ more significantly from [1,1,1]. Comparing C to A rather than comparing C to I, may therefore be more effective for some patients. If the comparison is based on A, then A is preferably updated at step 364 to incorporate the latest value of C. In this manner, A is frequently adjusted so as to properly represent the particular patient. If the specific manner of making the given change in is posture begins to change for the patient, perhaps as result of a loss of strength, the stored value for A is thereby automatically updated to ensure continued reliable change in posture detection. In any case, following steps 360 or 364, processing ultimately returns to FIG. 4 to take into account whether a close match has been detected.

Thus FIGS. 4–7 illustrate a technique for detecting a particular change in posture. In the following, a more general technique fir discriminating among an entire set of possible changes in posture is described.

General Patient Posture Discrimination Technique

Figure 8:
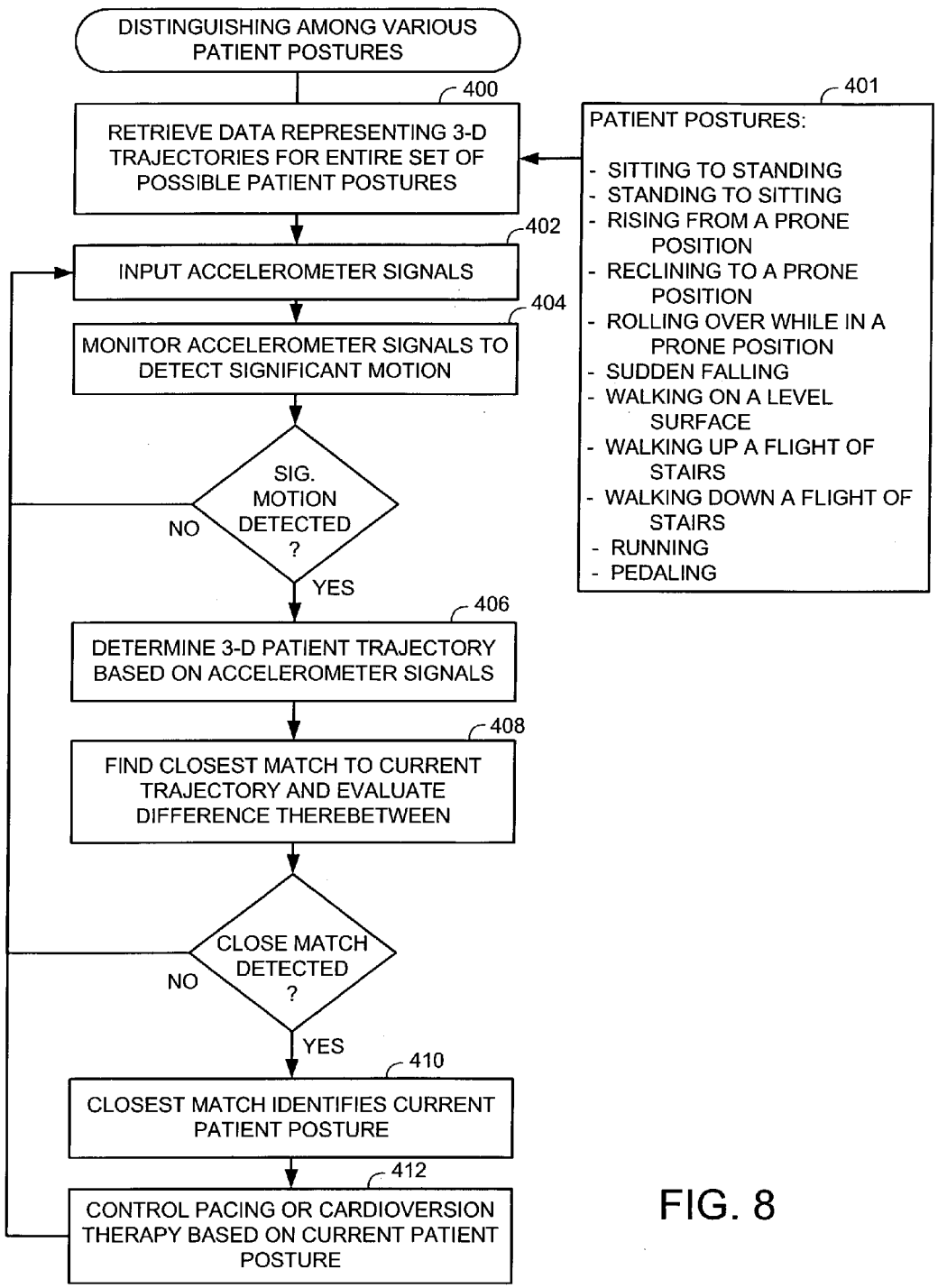
FIG. 8 is a flow chart providing an overview of a second exemplary technique performed by the posture determination system of FIG. 2, particularly directed toward discriminating among numerous possible postures or changes in posture based on 3D spatial trajectories of the patient.
Figure 9:
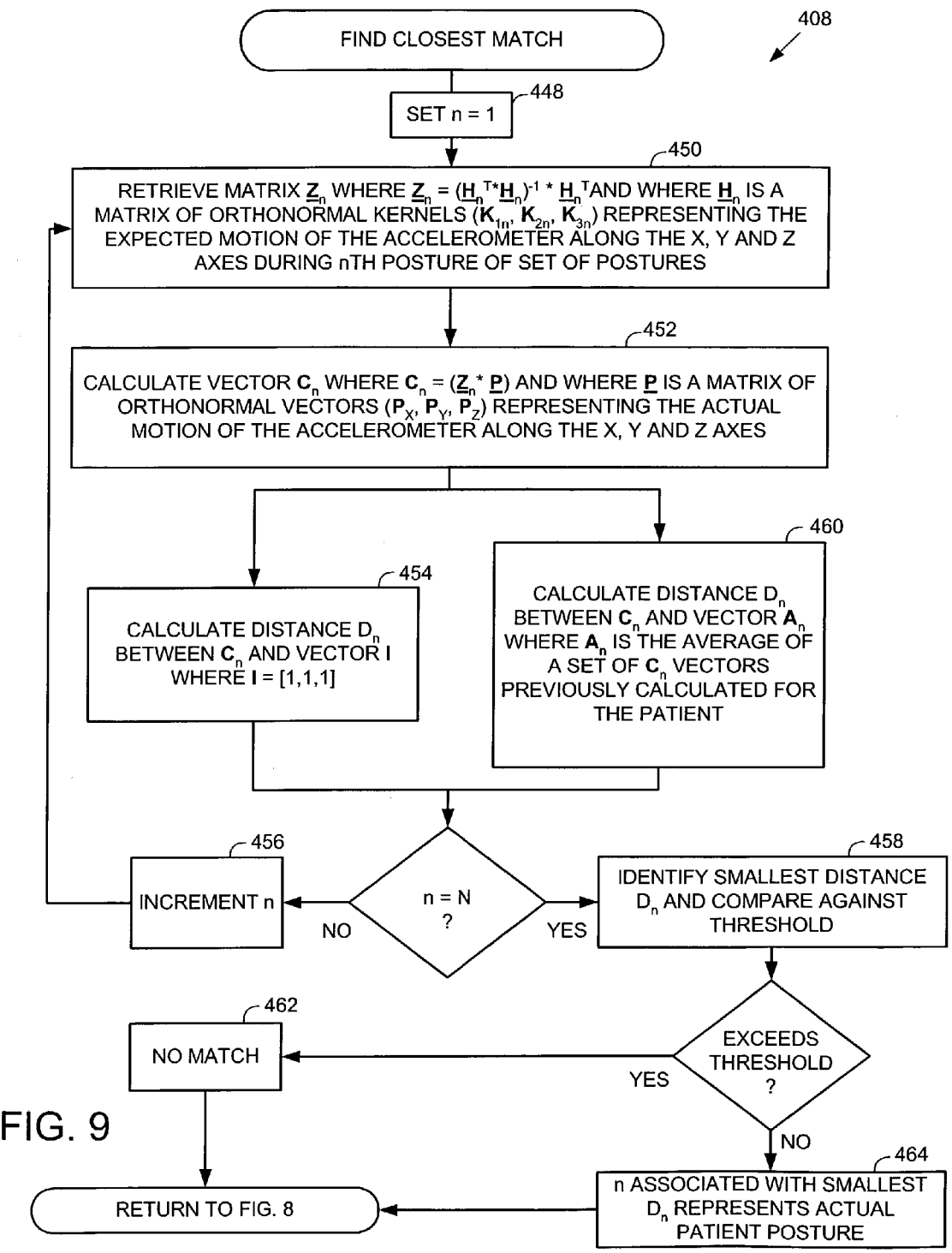
FIG. 9 is a flow chart illustrating, in detail, a best match identification method performed as part of the technique of FIG. 8 for finding the closest match between the actual 3D trajectory of the patient and a set of expected 3D trajectories corresponding to a set of possible changes in posture based, in part, on a set of pre-calculated comparison matrices $Z_n$.

FIG. 8 provides an overview of a general patient posture discrimination technique performed by the in posture detection system 101 of FIG. 2. The technique operates to detect whether any one of set of possible patient postures is occurring, such as the set of dynamic postures and changes in posture listed in TABLE I, above. FIG. 9 provides a detailed example of one particular technique for finding a closest match among a set of patient posture. The general technique of FIGS. 8 and 9 is similar to that of the individual technique of FIGS. 4–7 and only pertinent differences will be described in detail.

Initially, at steps 400 and 401, the device retrieves data representing expected 3-D trajectories for a set of patient postures. At steps 402 and 404, the device inputs accelerometer signals and monitors the signals to detect any significant new motion consistent with a change in posture. Once significant motion is detected, the device, at step 406, determines the actual 3-D trajectory of the chest of the patient by integrating the accelerometer signals. At step 408, the device compares the actual 3-D trajectory of the chest with each of the expected 3-D trajectories retrieved at step 400 to find the closest match and to evaluate whether the closest match is sufficiently close to warrant the conclusion, at step 410, that the corresponding change in posture has just occurred or that the corresponding dynamic posture is on-going. If so, then, at step 412, the device adjusts its functions in response to the detected patient posture, for example, to temporarily increase the pacing rate as needed or to inhibit cardioversion shocks.

Thus, the technique of FIG. 8 operates to identify the current patient posture out of a set of possible patient postures. As with the technique of FIG. 4, preferably a matrix-based technique is employed (at step 408) for evaluating the differences between the actual patient trajectory and the expected trajectories associated with each of the various possible patient postures. This generalized matrix technique will now be described with reference to FIG. 9. FIG. 9 will be described with reference to an example wherein a change is posture is to be detected but, as with the technique of FIG. 6, the technique of FIG. 9 is also applicable to detection of an on-going dynamic posture.

The technique of FIG. 9 essentially operates to solve the matrix equation $P=H_n*C_n$ for $C_n$ for each value of n wherein n=1, 2, . . . N represents the number of possible patient postures. As before, P is a matrix of time-series values representing the actual trajectory of the patient. $H_n$ is a matrix of time-series values representing the expected trajectory of the patient for the nth change in posture, and wherein $C_n$ is a correction vector representing any differences between the actual trajectory and the expected trajectory of the nth change in posture. Again, rather than requiring the implanted device itself to solve the matrix equations $P=H_n*C_n$ for each possible change in posture by solving $C_n=(H_n^T*H_n)^{-1}*H_n^T*P$, which is a computationally intensive procedure, the values of $(H_n^T*H_n)^{-1}*H_n^T$ are pre-calculated for each n and stored in the implantable device as a set of comparison matrices $Z_n$ wherein $Z_n=(H_n^T*H_n)^{-1}*H_n^T$. Hence, the device need only perform the considerably less computationally intensive procedure of calculating $Z_n*P$ to yield each correction vector $C_n$. Also as before, rather than representing the expected to trajectory for the change in posture in terms of actual raw trajectory data stored within matrix $H_n$, $H_n$ is instead initially represented using a set of idealized orthonormal kernels $(K_{1n}, K_{2n}, K_{3n})$ each representing the expected motion of the accelerometer along one of the orthogonal axes in terms of coefficients to Laguerre functions or Lagrange functions.

Initially, at step 448, n is set to 1, for processing based on the first of the set of possible changes in posture. At step 450, the device retrieves pre-calculated comparison matrix $Z_1$ from memory wherein $Z_1=(H_1^T*H_1)^{-1}*H_1^T$ and $H_1$ is the matrix of orthonormal kernels $(K_{11}, K_{21}, K_{31})$ representing the expected motion of the accelerometer along three orthonormal axes during the first change in posture to be evaluated. At step 452, the device calculates vector $C_1$ by performing the matrix multiplication $Z_1*P$. The device then determines how closely the actual trajectory (P) matches the expected trajectory $(H_1)$ by calculating the distance between $C_1$ and I, at step 454, which is then represented as $D_1$. Hence, the closer the actual trajectory P is to the expected trajectory $H_1$, the closer $C_1$ will be to I and therefore the closer $D_1$ will be to 0. Thus, the magnitude of $D_1$ represents the extent to which the actual trajectory matches the expected trajectory for the first change in posture being evaluated.

At step 456, n is incremented and steps 450–454 are repeated to calculate a separate $D_n$ for each change in posture n. Once a value for $D_n$ has been calculated for each change in posture then, at step 458, the smallest $D_n$ is identified at step 458, which represents the closest match. For example, if $D_3$ is the smallest of the calculated D values, then the change in posture identified by n=3 represents the closest match. As an alternative, rather than deriving $D_n$ by calculating the distance between $C_n$ and I (at step 454), the device instead derives each $D_n$ by calculating the distance between $C_n$ and an average vector $A_n$, at step 460. $A_n$ is the average or centroid of a set of previously calculated $C_n$ vectors determined for the patient while repeatedly undergoing the nth change in posture. Hence, the closer $C_n$ is to $A_n$, the closer $D_n$ is to 0, and the more likely the current change in posture matches the nth change in posture.

In either case, once all values for n have been processed, then the smallest $D_n$ is identified at step 458 and compared to a threshold representative of a sufficiently close match. If the smallest $D_n$ exceeds the threshold, then no match is declared at step 464. If however the smallest $D_n$ falls within the threshold, then the n associated with the smallest $D_n$ is declared to be representative of the current change in posture, at step 464. Although not shown, the values for $A_n$ for the detected change in posture may be updated using $C_n$. In other words, if n=3 represents the detected change in posture, then $A_3$ is updated based on $C_3$. Other values for $A_3$ are not adjusted. In any case, processing ultimately returns to FIG. 8 to take into account the detected change in posture or on-going dynamic posture.

What have been described thus far are various techniques for automatically determining patient posture using a trajectory-based posture detection system implemented within an implantable medical device. The examples above pertain to implantable cardiac stimulation devices. However, the posture detection system can be employed in connection with other implantable medical devices or may be used as an independent implantable medical device. As noted above, for efficiency, certain matrices and vectors are calculated in advance to reduce the processing burden of the posture detection system itself. In the following, techniques are described for pre-calculating these vectors and matrices using an external programmer device or other external processing system.

Set-Up Technique

Figure 10:
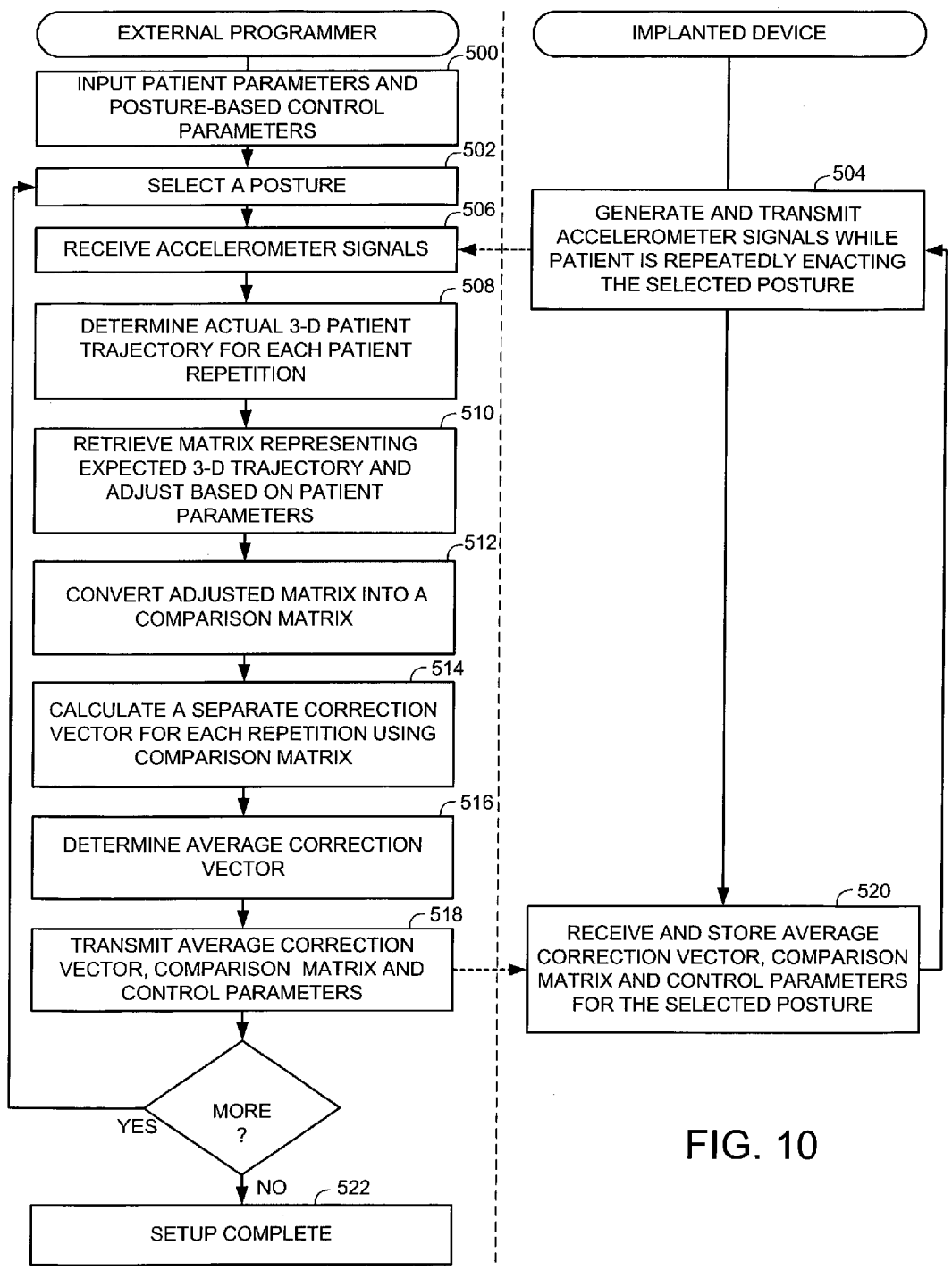
FIG. 10 is a flow chart providing an overview of a set-up technique performed primarily by the setup system of the external programmer of FIG. 3 for pre-calculating correction vectors, comparison matrices and other information for transmitting to the implantable device of FIG. 2 to facilitate the posture determination techniques employed therein.

FIG. 10 primarily illustrates steps performed by posture detection set-up system 250 of FIG. 4. FIG. 10 also illustrates associated steps performed by the implanted device, with the external programmer steps shown on the left and implantable device steps shown on the right. Initially, at step 500, the set-up system inputs patient parameters such as name, age, gender, height and weight, and, depending upon the implementation, specific physical dimensions of the patient such as torso length, leg length etc, which, as will be explained below, are used for retrieving data appropriate to the particular patient. Data is input by the physician or other medical personnel operating the external programmer. The physician also input control parameters specifying steps, if any, to be taken by the implanted device upon detection of particular patient postures. For example, the physician may specify that cardioversion therapy is to be inhibited whenever the patient is found to be walking up or down stairs, running or pedaling. At step 502, the physician selects a patient posture from a pre-programmed list of patient postures (such as those listed above in TABLE I.) Once a particular patient posture has been selected, the physician instructs the patient to repeatedly perform the selected change in posture or, in the case of a dynamic posture, such as running, the physician instructs the patient to engage in that activity, preferably on a treadmill. Thus, if the physician has selected the change in posture of rising from a seated position to a standing position, the patient will then repeatedly perform that change in posture. While the patient is repeatedly performing the change in posture, the posture detection system of the implantable device, at step 504, generates and transmits accelerometer signals to the external programmer. Note that, unlike with the techniques described above, the posture detection system of the implantable device does not attempt to detect patient posture nor does the system attempt to calculate the aforementioned correction vectors C. Rather, the posture detection system merely transfers the raw accelerometer signals $(a_x(t), a_y(t)$ and $a_y(t))$ to the set-up system, which are received and stored at step 506. The raw accelerometer signals are separately stored for each repetition, thus providing multiple sets of signals $(a_{xm}(t), a_{ym}(t)$ and $a_{zm}(t))$ for m=1, 2 . . . M where M is the total number of repetitions for the selected patient posture and where it is to be understood that each acceleration signal, such as $a_{xm}(t)$ is composed of a plurality of samples of individual acceleration values.) Depending upon the implementation, the set-up system may be configured to receive accelerometer signals only while the patient is engaged in the selected change in posture (as indicated by entry of appropriate commands by the physician.) Alternatively, the set-up system may be configured to input all accelerometer signals generated within the period of time while the patient is repeatedly performing the selected change in posture. If so, the set-up system is provided with software tools for the deleting, either automatically or under the control physician, accelerometer signals not generated while the patient is actually performing the selected change in posture. In this manner, accelerometer signals generated while the patient is moving from the standing position to the seated position are properly ignored and the only signals that are stored are those generated during the actual selected change in posture.

At step 508, the set-up system then integrates the raw accelerometer signals to determine the actual three-dimensional trajectory for the patient during each repetition, with the 3-D trajectories being stored separately as separate trajectory vectors. Thus the set-up system generates a set of trajectory 3-D matrices $P_m$ for m=1, 2 . . . M where $P_m=[a_{xm}(t), a_{ym}(t)$ and $a_{zm}(t)]$. Preferably, the patient is instructed to perform the selected change in posture some fixed number of times (e.g. ten times), thereby permitting generation of an equal number of 3-D patient trajectory matrices. For on-going dynamic postures, such as running, the patient is preferably instructed to run for some fixed period of time (e.g. at least one minute), with separate trajectories periodically recorded during that period of time. In any case, at step 510, the set-up system then retrieves from memory an $H_n$ matrix representing expected 3-D trajectories for the selected patient posture n (where there are N total possible patient postures to be selected from, at step 502) for patients similar to the particular patient under consideration. As before, the $H_n$ matrix consists of orthonormal kernels $[K_{1n}, K_{2n}, K_{3n}]$ preferably represented using the Laguerre or Lagrange functions. The $H_n$ matrix may be generated in advance based on data derived from a population of patients. Preferably, numerous $H_n$ matrices are stored representative of the expected trajectories for various patients of different height, weight, and gender, etc. The set-up system uses the patient parameters initially input at step 500 to select the particular $H_n$ matrix appropriate for use with the current patient. If the patient data input at step 500 includes actual physical dimensions of the legs and torso of the patient, this information can be used also to select for the $H_n$ matrix most representative of the current patient. Alternatively, a single $H_n$ matrix is stored and is modified if needed based on the physical dimension parameters of the patient input at step 500. In any case, once the appropriate $H_n$ matrix has been retrieved or generated, the set-up system then generates, at step 512, the corresponding $Z_n$ matrix at step 512 by calculating $(H_n^T * H_n)^{-1} * H_n^T$. This is a fairly processor intensive operation, requiring the transposition of the $H_n$ matrix. By performing this calculation using the external programmer, the posture detection system of the implanted device need not perform the calculation itself.

At step 514, the set-up system calculates, for each of the M repetitions of the change in posture, a correction vector $C_{mn}$ representative of the difference between the actual trajectory of the patient generated during the repetition and the typical trajectory represented by the $H_n$ matrix by calculating $C_{mn}=Z_n*P_m$. At step 516, the set-up system then determines an average vector $A_n$ based on the entire set of $C_{mn}$ vectors (i.e. all M vectors). This may be achieved using any appropriate averaging technique such as by calculating the centroid of the set of $C_{mn}$ vectors. At step 518, the set-up system transmits the averaged correction vector $A_n$ and the matrix $Z_n$ to the implantable device along with an identification of the particular change in posture (n). The set-up system also transmits any control parameters entered by the physician at step 500. The transmitted data is received by the implanted device at step 520 and stored within memory for subsequent used by the posture determination system in accordance with the techniques already described. Note that if the posture detection system determines patient posture based on a comparison with the identity vector I (i.e. step 354 of FIG. 6) rather than the average vector $A_n$ (i.e. step 362 of FIG. 6), then the average vector $A_n$ need not be calculated by the set-up system nor stored by the implanted device.

In any case, following step 518, processing returns to step 502 for selection of another patient posture to be processed. For example, the physician may then have the patient repeatedly perform the change in posture associated with sitting down from a standing position. Again, the set-up system retrieves accelerometer signals from the implanted device detected while the patient is repeatedly performing the new patient posture and proceeds to automatically calculate a new Z matrix and a new A correction vector for the new patient posture based on the motion of the particular patient. Steps 502–518 are performed as many times as needed to generate the vectors and matrices associated with any number of selected patient postures. Once the last patient posture has been fully processed, the set up process is complete, step 522.

Thus, FIG. 10 provides technique for pre-calculating Z matrices and A vectors so that the implanted device may thereafter utilize these matrices and vectors during detection of changes in posture, in accordance with the techniques described above in connection with FIGS. 5–9. By pre-calculating this information, the processing burden of the implanted device is reduced. Moreover, the implanted device need not store the many possible H matrices representative of different patient characteristics. In addition, the technique allows the physician to control the response of the implanted device to various detected patient postures.

What have been described are various techniques for detecting patient posture using an implantable medical device and for pre-calculating information within an external programmer for subsequent use by the implantable medical device in the detection of posture. In general, the embodiments described herein are merely illustrative of the invention and should not be construed as limiting the scope of the invention, which is to be interpreted in accordance with the claims that follow.

What is claimed is:

1. For use in an implantable medical device for implant within a patient, a method comprising:
    storing one or more trajectory templates in memory;
    detecting time-varying signals representative of a trajectory of the patient;
        generating a trajectory based on the time-varying signals; and
        identifying patient posture based on a comparison of the trajectory with the one or more trajectory templates.

2. The method of claim 1 wherein identifying patient posture comprises:
    retrieving information representative of trajectories associated with selected postures of interest; and
    identifying patient posture from the time-varying signals representative of the trajectory of the patient in combination with the information representative of trajectories associated with the postures of interest.

3. The method of claim 1 wherein the time-varying signals are time-varying 3-D acceleration signals.

4. The method of claim 3 wherein identifying patient posture comprises:
  integrating the time-varying 3-D acceleration signals to derive time-varying 3-D position signals; and
  identifying patient posture based on the time-varying 3-D position signals.

5. The method of claim 1 wherein identifying patient posture based on the time-varying signals further comprises identifying a change in posture.

6. The method of claim 1 wherein identifying patient posture based on the time-varying signals comprises:
  retrieving information representative of 3-D spatial trajectories associated with a posture of interest in the form of a comparison matrix Z wherein $Z=(H^T*H)^{-1}*H^T$ where H is a matrix of orthonormal kernels ($K_1$, $K_2$, $K_3$) each representing the expected motion of the patient along an orthonormal axis;
  integrating the time-varying signals representative of the trajectory of the patient to yield a matrix P of orthonormal vectors ($P_1$, $P_2$, $P_3$) each representing the actual motion of the patient along a respective orthonormal axis; and
  determining whether the actual patient posture corresponds to the posture of interest by determining whether P sufficiently matches H by evaluating a correction vector C wherein $C=Z*P$.

7. The method of claim 6 wherein determining whether P sufficiently matches H comprises:
  calculating a distance D of the correction vector C from a vector I wherein $I=[1,1,1]$; and
  determining whether the distance D is less than a predetermined threshold distance.

8. The method of claim 6 wherein determining whether P sufficiently matches H comprises:
  calculating a distance D of the correction vector C from a pre-stored vector A, wherein A represents a pre-calculated average of a corresponding vector C for the particular patient in which the stimulation device is implanted; and
  determining whether the distance D is less than a predetermined threshold distance.

9. The method of claim 1 further comprising:
  controlling operation of the implantable medical device based on the identified posture.

10. The method of claim 9 wherein the implantable medical device comprises an implantable cardiac stimulation device operative to deliver pacing pulses for delivery to the heart of the patient and wherein controlling operation of the implantable medical device based on the identified posture comprises selectively adjusting a pacing rate based in patient posture.

11. The method of claim 9 wherein the implantable medical device comprises an implantable cardiac stimulation device operative to deliver shocking pulses for delivery to the heart of the patient and wherein controlling operation of the implantable medical device based on the identified posture comprises selectively inhibiting shocking pulses based on patient posture.

12. The method of claim 11 wherein selectively inhibiting shocking pulses based on patient posture comprises inhibiting delivery of shocking pulses while the patient is in a posture associated with walking up stairs, walking down stairs, running or pedaling.

13. In an implantable medical device for implant within a patient, a system comprising:
  a memory operative to store information representative of trajectories associated with a posture of interest;
  an accelerometer operative to detect time-varying signals representative of an actual trajectory of the patient; and
  a trajectory-based posture determination system operative to identify patient posture by generating a trajectory from a plurality of temporally-spaced ones of the time-varying signals and by comparing the trajectory with the information representative of trajectories associated with the posture of interest.

14. The system of claim 13
  wherein the memory stores information representative of 3-D spatial trajectories associated with a particular posture of interest in the form of a comparison matrix Z wherein $Z=(H^T*H)^{-1}*H^T$ where H is a matrix of orthonormal kernels ($K_1$, $K_2$, $K_3$) each representing the motion of the accelerometer along an orthonormal axis expected to be associated with the particular posture of interest;
  wherein the posture determination system integrates the time-varying spatial signals representative of the actual 3-D trajectory of the patient to yield a matrix P of orthonormal vectors ($P_1$, $P_2$, $P_3$) each representing the actual motion of the accelerometer along a respective orthonormal axis; and
  wherein the posture determination system determines whether the actual patient posture corresponds to the particular posture of interest by determining whether P sufficiently matches H by evaluating a correction vector C wherein $C=Z*P$.

15. The system of claim 14 wherein the posture determination system determines whether P sufficiently matches H by calculating a distance D of the correction vector C from a vector I wherein $I=[1,1,1]$ and then determining whether the distance D is less than a predetermined threshold distance.

16. The system of claim 14 wherein the posture determination system determines whether P sufficiently matches H by calculating a distance D of the correction vector C from a pre-stored vector A, wherein A represents a pre-calculated average of a corresponding vector C for the particular patient in which the stimulation device is implanted, and then determining whether the distance D is less than a predetermined threshold distance.

17. The system of claim 14 wherein the idealized orthonormal kernels ($K_1$, $K_2$, $K_3$) are represented by one or more of Laguerre functions and Lagrange functions.

18. The system of claim 13 wherein the posture determination system is further operative to control operation of the implantable medical device based on the identified posture.

19. The system of claim 18 wherein the implantable medical device comprises an implantable cardiac stimulation device operative to deliver pacing pulses for delivery to the heart of the patient and wherein the posture determination system selectively adjusts a pacing rate based in patient posture.

20. The system of claim 13 wherein the implantable medical device comprises an implantable cardiac stimulation device operative to deliver shocking pulses for delivery to the heart of the patient and wherein the posture determination system selectively disables shocking pulses based on patient posture.

21. The system of claim 20 wherein the posture determination system disables delivery of shocking pulses while the patient is in a posture associated with walking up stairs, walking down stairs, running or pedaling.

22. A system for use with an implantable medical device for implant within a patient, the system comprising:
  means for storing information representative of 3-D trajectories associated with a posture of interest;
  means for detecting time-varying signals representative of an actual 3-D trajectory of the patient;
  means for generating a trajectory based on the time-varying signals; and
  means for identifying patient posture by comparing the trajectory with 3-D trajectories associated with the posture of interest.

* * * * *